United States Patent
Holton et al.

(10) Patent No.: US 7,589,111 B2
(45) Date of Patent: Sep. 15, 2009

(54) C10 CYCLOPENTYL ESTER SUBSTITUTED TAXANES

(75) Inventors: Robert A. Holton, Tallahassee, FL (US); Phong Vu, Little Falls, NJ (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 696 days.

(21) Appl. No.: 11/057,703

(22) Filed: Feb. 14, 2005

(65) Prior Publication Data

US 2005/0228037 A1    Oct. 13, 2005

Related U.S. Application Data

(60) Provisional application No. 60/544,755, filed on Feb. 13, 2004, provisional application No. 60/613,503, filed on Sep. 27, 2004.

(51) Int. Cl.
- A61K 31/38 (2006.01)
- A61K 31/335 (2006.01)
- C07D 305/00 (2006.01)
- C07D 405/00 (2006.01)

(52) U.S. Cl. .................. 514/337; 514/444; 514/449; 514/471; 549/60; 549/510; 549/511; 546/281.7

(58) Field of Classification Search ............... 549/510, 549/511, 60; 546/281.7; 514/449, 444, 471, 514/337

See application file for complete search history.

(56) References Cited

U.S. PATENT DOCUMENTS

| | | | |
|---|---|---|---|
| 4,814,470 A | 3/1989 | Colin et al. | |
| 5,175,315 A | 12/1992 | Holton | |
| 5,200,534 A | 4/1993 | Rao | |
| 5,227,400 A | 7/1993 | Holton et al. | |
| 5,243,045 A | 9/1993 | Holton et al. | |
| 5,250,683 A | 10/1993 | Holton et al. | |
| 5,254,580 A | 10/1993 | Chen et al. | |
| 5,274,124 A | 12/1993 | Holton | |
| 5,283,253 A | 2/1994 | Holton et al. | |
| 5,350,866 A | 9/1994 | Holton et al. | |
| 5,367,086 A | 11/1994 | Rao | |
| 5,407,674 A | 4/1995 | Gabetta et al. | |
| 5,430,160 A | 7/1995 | Holton | |
| 5,475,011 A | 12/1995 | Ojima et al. | |
| 5,556,878 A | 9/1996 | Kelley et al. | |
| 5,567,614 A | 10/1996 | Patel et al. | |
| 5,614,645 A | 3/1997 | Kingston et al. | |
| 5,714,512 A | 2/1998 | Bastart et al. | |
| 5,714,513 A | 2/1998 | Holton et al. | |
| 5,721,268 A | 2/1998 | Holton et al. | |
| 5,739,362 A | 4/1998 | Holton et al. | |
| 5,756,776 A | 5/1998 | Bombardelli et al. | |
| 5,767,297 A | 6/1998 | Mandai et al. | |
| 5,780,653 A | 7/1998 | Tao et al. | |
| 5,811,452 A | 9/1998 | Ojima et al. | |
| 5,879,929 A | 3/1999 | Patel | |
| 5,889,043 A | 3/1999 | Bouchard et al. | |
| 5,906,990 A | 5/1999 | Bouchard et al. | |
| 5,912,264 A | 6/1999 | Wittman et al. | |
| 5,959,125 A | 9/1999 | Bouchard et al. | |
| 5,965,739 A | 10/1999 | Kelly et al. | |
| 6,156,789 A | 12/2000 | Bissery et al. | |
| 6,268,381 B1 | 7/2001 | Shimizu et al. | |
| 6,369,244 B1 | 4/2002 | Holton et al. | |
| 6,638,973 B2 | 10/2003 | Holton | |
| 6,649,632 B2 | 11/2003 | Holton | |
| 6,660,866 B2 | 12/2003 | Holton | |
| 6,780,879 B2 | 8/2004 | Holton | |
| 2001/0002404 A1 | 5/2001 | Webb et al. | |

FOREIGN PATENT DOCUMENTS

| | | |
|---|---|---|
| EP | 0 537 709 B1 | 3/1993 |
| EP | 0 558 959 B1 | 9/1993 |
| EP | 0 590 267 A2 | 4/1994 |
| EP | 0 590 267 A3 | 4/1994 |
| EP | 0 600 517 B1 | 6/1994 |
| EP | 0 604 910 B1 | 7/1994 |
| EP | 0 629 701 B1 | 12/1994 |
| EP | 0 639 577 B1 | 2/1995 |
| EP | 0882732 B1 | 3/2004 |
| WO | 9306079 A1 | 4/1993 |
| WO | WO 93/18018 A1 | 9/1993 |
| WO | WO 93/23389 A1 | 11/1993 |
| WO | WO 94/07880 A1 | 4/1994 |
| WO | WO 94/13655 A1 | 6/1994 |
| WO | WO 94/20484 A1 | 9/1994 |

(Continued)

OTHER PUBLICATIONS

International Search Report for PCT Application No. PCT/US01/03623 dated Jun. 8, 2001.
European Search Report for EP Application No. 01118728 dated Nov. 14, 2001.
Georgian Search Report for AP 2001 004523 dated Feb. 26, 2003.
Journal of Chinese Universities, (2000), pp. 401-406, vol. 21:3.
Journal of Tianjin University, (2000), pp. 51-55, vol. 33:1.
European Search Report for EP Application No. 05713407 dated Oct. 23, 2007.
Singapore Search Report for SG Application No. 200605379-7 dated Sep. 18, 2007.
International Search Report for PCT Application No. PCT/US06/04914 dated Sep. 28, 2007.
Deepak Sampath et al., MST-997: A novel taxane with superior efficacy that overcomes paclitaxel and docetaxel resistance in vitro and in vivo, Abstract # 524 Presented at the 2004 Joint Meeting of EORTC-NCI-AACR, Geneva, Switzerland, Sep. 28-Oct. 1, 2004.

(Continued)

*Primary Examiner*—Janet L. Andres
*Assistant Examiner*—Raymond Covington
(74) *Attorney, Agent, or Firm*—Bryan Cave LLP

(57) ABSTRACT

A taxane having a cyclopentyl ester substituent at C10, a keto substituent at C9, a hydroxy substituent at C2, a 2-thienyl substituent at C3' and an isopropoxycarbamate substituent at C3'.

17 Claims, 7 Drawing Sheets

FOREIGN PATENT DOCUMENTS

| WO | WO 95/04154 A1 | 2/1995 |
|---|---|---|
| WO | 9614308 A1 | 5/1996 |
| WO | WO 96/13495 A1 | 5/1996 |
| WO | WO 96/30356 A1 | 10/1996 |
| WO | WO 97/07110 A1 | 2/1997 |
| WO | WO 97/09979 A1 | 3/1997 |
| WO | WO 97/32578 A1 | 9/1997 |
| WO | WO 97/42181 A1 | 11/1997 |
| WO | WO 97/44026 A1 | 11/1997 |
| WO | WO 97/44063 A1 | 11/1997 |
| WO | WO 98/02426 A1 | 1/1998 |
| WO | WO 99/09021 A1 | 2/1999 |
| WO | WO 99/14209 A1 | 3/1999 |
| WO | WO 99/32473 A1 | 7/1999 |
| WO | WO 00/53592 A1 | 9/2000 |
| WO | WO 01/57013 A1 | 8/2001 |
| WO | WO 01/57032 A1 | 8/2001 |
| WO | WO 01/68089 A1 | 9/2001 |

OTHER PUBLICATIONS

Ross E. Longley et al., In vitro mechanism of action studies with the taxane analog, TL-909 (MSZT-997), Abstract Presented at the 95th Annual Meeting of the American Association for Cancer Research, Orlando Florida, Mar. 27-31, 2004.

International Search Report from PCT/US05/04442 dated Sep. 12, 2005.

Appendino, G. et al., "Synthesis of Paclitaxel (Docetaxel) / 2-Deacetoxytaxinine J Dimers", *Tetrahedron*, (1999), pp. 6567-6576, vol. 55.

Cravallee, C. et al., "Methyleniminium Salts as Acylating Agent—One Step Synthesis of Baccatin III from 10-Deacetylbaccatin III with High Selectivity", *Tetrahedron Letters*, (1998), pp. 4263-4266, vol. 39.

Dubois, J. et al., "Fluorescent and Biotinylated Analogues of Docetaxel: Synthesis and Biological Evaluation", *Bioorganic & Medicinal Chemistry*, (1995), pp. 1357-1368, vol. 3:10.

Guenard, D. et al., "Effects of the Hydrophobicity of Taxoids on Their Interaction with Tubulin", *Bioorganic & Medicinal Chemistry*, (2000), pp. 145-156, vol. 8.

Gueritte-Voegelein,F. et al., "Relationships Between the Structure of Taxol Analogues and Their Antimitotic Activity", *Journal of Medicinal Chemistry*, (1991), pp. 992-998, vol. 34:3.

Ishihara, K. et al., "Scandium Trifluoromethanesulfonate as an Extremely Active Acylation Catalyst", *J. Am. Chem. Soc.*, (1995), pp. 4413-4414, vol. 117:15.

Kant, J. et al., "A Chemoselective Approach to Functionalize the C-10 Position of 10-Deacetylbaccatin III. Synthesis and Biological Properties of Novel C-10 Taxol Analogues", *Tetrahedron Letters*, (1994), pp. 5543-5546, vol. 35:30.

Kirikae, T. et al., "Structural Significance of the Acyl Group at the C-10 Position and the A Ring of the Taxane Core of Paclitaxel for Inducing Nitric Oxide and Tumor Necrosis Factor Production by Murine Macrophages", *FEBS Letters*, (2000), pp. 221-226, vol. 478.

Kirikae, T. et al., "Structural Requirements of Taxoids for Nitric Oxide and Tumor Necrosis Factor Production by Murine Macrophages", *Biochemical and Biophysical Research Communications*, (1996), pp. 227-235, vol. 227:1494.

Kobayashi, J. et al., "Modulation of Multidrug Resistance by Taxuspine C and Other Taxoids from Japanese Yew", *Bioorganic & Medicinal Chemistry Letters*, (1998), pp. 1555-1558, vol. 8.

Lin, S. et al., "Synthesis of Highly Potent Second-Generation Taxoids Through Effective Kinetic Resolution Coupling of Racemic β-Lactams with Baccatins", *Chirality*, (2000), pp. 431-441, vol. 12.

Ojima, I. et al., "Synthesis and Structure—Activity Relationships of the Second-Generation Antitumor Taxoids: Exceptional Activity Against Drug-Resistant Cancer Cells", *J. Med. Chem.*, (1996), pp. 3889-3896, vol. 39:20.

Ojima, I. et al., "Synthesis and Biological Activity of Novel 3'-Trifluoromethyl Taxoids", *Bioorganic & Medicinal Chemistry*, (1997), pp. 133-138, vol. 7:2.

Ojima, I. et al., "Synthesis of Novel 3'-Trifluoromethyl Taxoids Through Effective Kinetic Resolution of Racemic 4-$CF_3$-β-Lactams With Baccatins", *Chirality*, (1997), pp. 487-494, vol. 9.

Ojima et al. "Efficient Asymmetric Synthesis of β-Lactams Bearing A Cyclopropane or an Epoxide Moiety and Their Application to the Synthesis of Novel Isoserines and Taxoids" Journal of Organic Chemistry, vol. 63, No. 2 (1998) pp. 224-225.

Ojima, I. et al., "New Photoaffinity Analogs of Paclitaxel", *Bioorganic & Medicinal Chemistry Letters*, (1999), pp. 1189-1194, vol. 9.

Ojima, I. et al., "Enantiopure Fluorine-Containing Taxoids: Potent Anticancer Agents and Versatile Probes for Biomedical Problems", *Journal of Fluorine Chemistry*, (1999), pp. 3-10, vol. 97.

Ojima, I. et al., Synthesis and Structure-Activity Relationships of New Second-Generation Taxoids, *Bioorganic & Medicinal Chemistry Letters*, (1999), pp. 3423-3428, vol. 9.

Ojima, I. et al., "Synthesis and Biological Activity fo C-3'-Difluoromethyl-Taxoids", *Bioorganic & Medicinal Chemistry*, (2000), pp. 1619-1628, vol. 8.

Rao, K.V. et al., "Synthesis and Evaluation of Some 10-Mono- and 2',10-Diesters of 10-Deacetylpaclitaxel", *J. Med. Chem.*, (1995), pp. 3411-3414, vol. 38:17.

Sengupta, S. et al., "Probing the Environment of Tubulin-Bound Paclitaxel Using Fluorescent Paclitaxel Analogues", *Biochemistry*, (1997), pp. 5179-5184, vol. 36:17.

Senilh, V. et al., "Mise en evidence de nouveaux analogues du taxol extraits de taxus baccata", *Journal of Natural Products*, (1984), pp. 131-137, vol. 47:1.

Shi, B-X et al., "Studies on the Quantitative Structure-Activity Relationships of Paclitaxel Analogues", *Chemical Journal of Chinese Universities*, (2000), pp. 401-406, vol. 21:3 (English Abstract attached).

Straubinger, R.M. et al., "Pharmacology and Antitumor Effect of Novel Placlitaxel Formulations" Chapter 8, *Taxane Anticancer Agents*, (1994), pp. 111-123.

Alley et al., Human Tumor Xenograft Models in NCI Drug Development, Anticancer Drug Development Guide, pp. 125-152 (Humana Press, Totowa, NJ, 2004).

Burger et al., Screening Using Animal Systems, Anticancer Drug Development, pp. 285-299 (Academic Press, San Diego, CA, 2002).

Fiebig et al., Human Tumor Xenografts and Explants, Tumor Models in Cancer Research 113-137 (Humana Press, Totowa, NJ, 2002).

Kingston et al., Bioactivity of Taxol and Other Taxoids, Progress in the Chemistry of Organic Natural Products 160-165 (Springer-Verlag, New York, 1993).

Rygaard et al., Heterotransplantation of a Human Malignant Tumor to "Nude" Mice, Acta Path. Microbiol. Scand. 77, 758-760, 1969.

Sampath et al., Preclinical Pharmacologic Evaluation of MST-997, an Orally Active Taxane with Superior In Vitro and In Vivo Efficacy in Paclitaxel- and Docetaxel-Resistant Tumor Models, Clinical Cancer Research 12(11), 3459-3469, 2006.

Suggitt et al., 50 Years of Preclinical Anticancer Drug Screening: Empirical to Target-Driven Approaches, Clin. Cancer Res. 11, 971-981, 2005.

C10 CYCLOPENTYL ESTER SUBSTITUTED TAXANES

CROSS-REFERENCE TO RELATED APPLICATIONS

This application claims priority from U.S. Provisional Application Ser. Nos. 60/544,755 and 60/613,503 filed Feb. 13, 2004 and Sep. 27, 2004, respectively, which are hereby incorporated by reference in their entirety.

BACKGROUND OF THE INVENTION

The present invention is directed to novel taxanes having utility as antitumor agents.

The taxane family of terpenes, of which baccatin III and taxol, also commonly referred to as paclitaxel, are members, has been the subject of considerable interest in both the biological and chemical arts. Taxol itself is employed as a cancer chemotherapeutic agent and possesses a broad range of tumor-inhibiting activity. Taxol has a 2'R, 3'S configuration and the following structural formula:

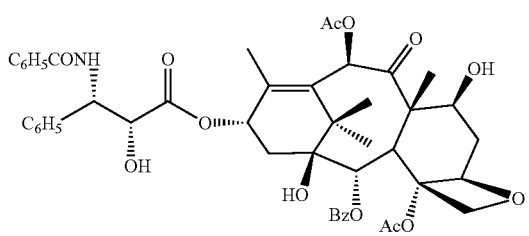

wherein Ac is acetyl and Bz is benzoyl.

Colin et al. reported in U.S. Pat. No. 4,814,470 that certain paclitaxel analogs have an activity significantly greater than that of taxol. One of these analogs, commonly referred to as docetaxel (Taxotere®), has the following structural formula:

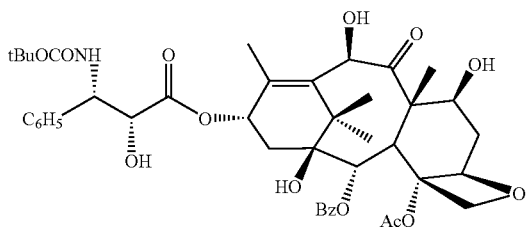

Although taxol and docetaxel are useful chemotherapeutic agents, there are limitations to their effectiveness, including limited efficacy against certain types of cancers and toxicity to subjects when administered at various doses. Accordingly, a need remains for additional chemotherapeutic agents with improved efficacy and less toxicity.

SUMMARY OF THE INVENTION

Among the various aspects of the present invention, therefore, is the provision of taxanes which compare favorably to taxol and docetaxel with respect to toxicity and to efficacy as an anti-tumor agent. In general, these taxanes possess a cyclopentyl ester substituent at C10, a keto substituent at C9, a hydroxy substituent at C7, a thienyl substituent at C3' and an isopropoxycarbamate substituent at C3'.

Briefly, therefore, the present invention is directed to taxanes, per se, to prodrugs thereof, to pharmaceutical compositions comprising the taxanes or prodrugs and a pharmaceutically acceptable carrier, to methods of treatment and administration, and to methods of preparation of medicaments comprising the taxanes or prodrugs.

Other objects and features of this invention will be in part apparent and in part pointed out hereinafter.

DETAILED DESCRIPTION OF THE PREFERRED EMBODIMENTS

Figure 1:
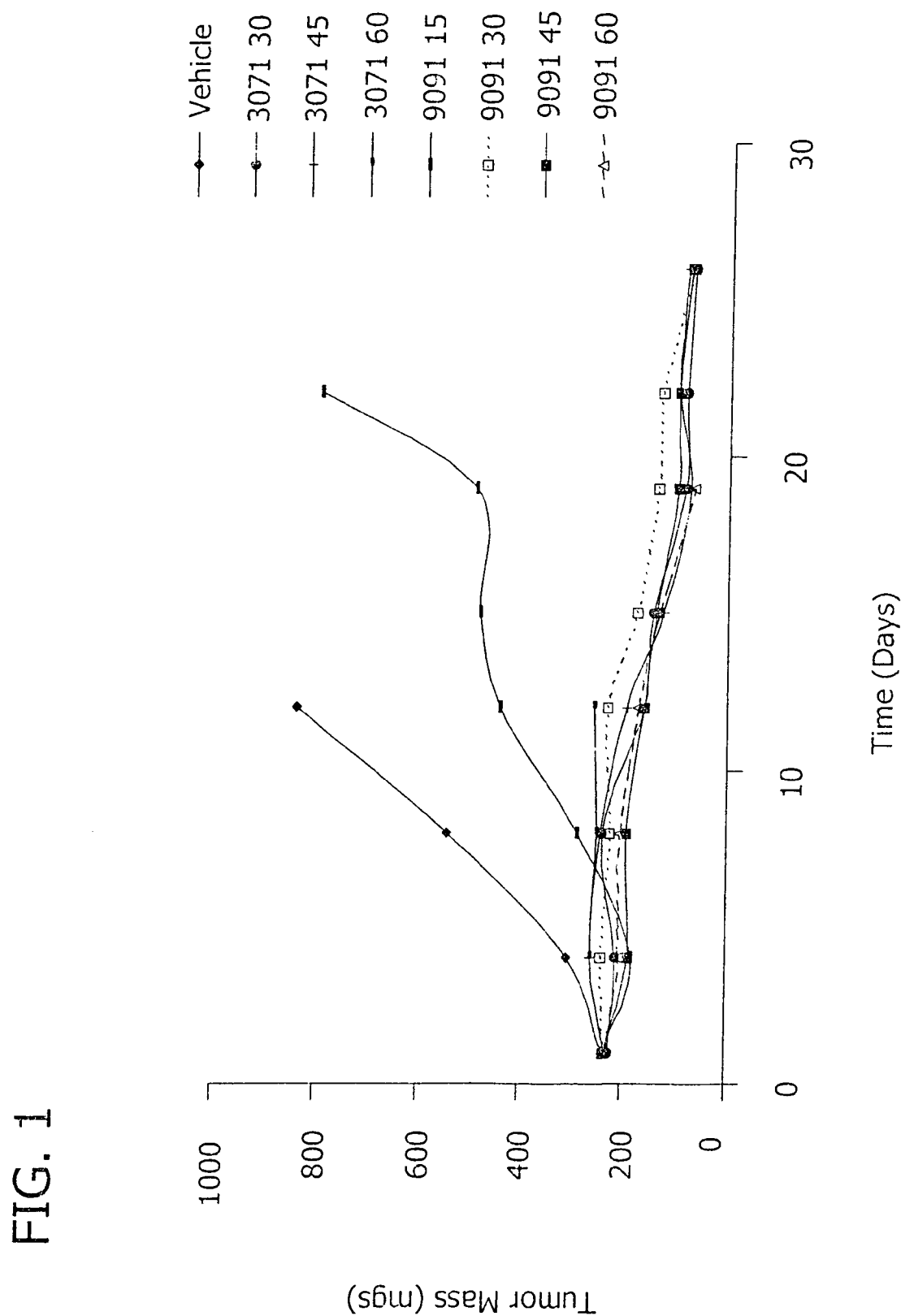
FIG. 1 depicts median tumor growth curves for mice treated with compound 9091 vs. compound 3071 in the Panc-1 study (oral q4d×4 doses).

The taxane of the present invention has the following chemical structure:

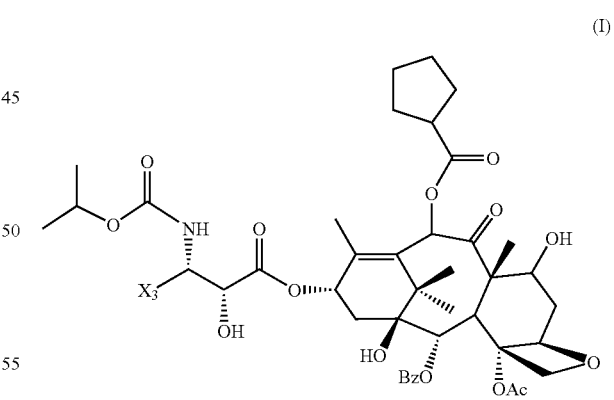

(I)

wherein $X_3$ is thienyl, Ac is acetyl and the C7 hydroxy substituent and the C10 cyclopentylcarbonyloxy substituent independently have the alpha or beta stereochemical configuration. In one embodiment, $X_3$ is 2-thienyl. In a preferred embodiment, $X_3$ is 2-thienyl and the C7 hydroxy substituent and the C10 cyclopentylcarbonyloxy substituent both have the beta stereochemical configuration.

Compounds of the present invention are active against cancers in a manner superior to conventionally used taxanes with respect to certain tumor types, including paclitaxel (taxol) sensitive and resistant tumor lines. The compounds of the present invention are reasonably well tolerated whether administered orally or intravenously and can be effective as a single or multiple dose with improved toxicity profiles. The compounds of the present invention are also efficacious in non-cremophor vehicles.

The taxanes of the present invention may be obtained by treatment of a β-lactam with an alkoxide having the taxane tetracyclic nucleus and a C13 metallic oxide substituent to form compounds having a β-amido ester substituent at C13 (as described more fully in Holton U.S. Pat. No. 5,466,834), followed by removal of the hydroxy protecting groups. The β-lactam has the following structural formula (1):

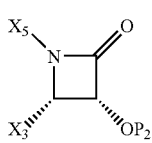

(1)

wherein $P_2$ is a hydroxy protecting group, $X_3$ is thienyl, and $X_5$ is isopropoxycarbonyl and the alkoxide has the structural formula (2):

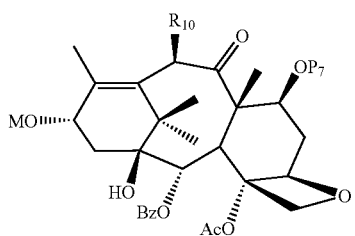

(2)

wherein M is a metal or ammonium, $P_7$ is a hydroxy protecting group and $R_{10}$ is cyclopentylcarbonyloxy.

The alkoxide of structural formula (2) may be prepared from 10-deacetylbaccatin III (or a derivative thereof) by selective protection of the C7 hydroxyl group and then esterification of the C10 hydroxyl group followed by treatment with a metallic amide. In one embodiment of the present invention, the C7 hydroxyl group of 10-deacetylbaccatin III is selectively protected with a silyl group as described, for example, by Denis, et. al. (*J. Am. Chem. Soc.*, 1988, 110, 5917). In general, the silylating agents may be used either alone or in combination with a catalytic amount of a base such as an alkali metal base.

Alternatively, the C10 hydroxyl group of a taxane can be selectively acylated in the absence of a base, as described, for example in Holton et al., PCT Patent Application WO 99/09021. Acylating agents which may be used for the selective acylation of the C10 hydroxyl group of a taxane include substituted or unsubstituted alkyl or aryl anhydrides. While the acylation of the C10 hydroxy group of the taxane will proceed at an adequate rate for many acylating agents, it has been discovered that the reaction rate may be increased by including a Lewis acid in the reaction mixture. Preferred Lewis acids include zinc chloride, stannic chloride, cerium trichloride, cuprous chloride, lanthanum trichloride, dysprosium trichloride, and ytterbium trichloride. Zinc chloride or cerium trichloride is particularly preferred when the acylating agent is an anhydride.

Processes for the preparation and resolution of the β-lactam starting material are generally well known in the art. For example, the β-lactam may be prepared as described in Holton, U.S. Pat. No. 5,430,160 (col. 9, lines 2-50) or Holton, U.S. Pat. No. 6,649,632 (col. 7, line 45-col. 8, line 60), which are both hereby incorporated by this reference in their entirety. The resulting enatiomeric mixtures of β-lactams may be resolved by a stereoselective hydrolysis using a lipase or enzyme as described, for example, in Patel, U.S. Pat. No. 5,879,929 (col. 16, lines 1-col. 18, line 27) or Patel, U.S. Pat. No. 5,567,614 or a liver homogenate as described, for example, in Holton, U.S. Pat. No. 6,548,293 (col. 3, lines 30-61). By way of example, U.S. Pat. No. 6,649,632 discloses the preparation of a β-lactam having a furyl substituent at the C4 position of the β-lactam. With modifications evident to those skilled in the art, a β-lactam having a thienyl substituent at the β-lactam C4 position may be prepared as illustrated in these prior patents and as further disclosed in Example 1.

The compounds of the present invention may be provided in the form of a prodrug. In general, a pharmaceutically acceptable derivative or prodrug is any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species. Pharmaceutically acceptable prodrugs include, but are not limited to, taxanes of the present invention derivatized with one or more of the following groups: phosphates, pivaloyloxymethyl, acetoxymethyl, phthalidyl, indanyl, methoxymethyl, methylpyridinium mesylate, bicarbonate, onium salts, phosphonooxymethyl carbonate, cinnamate, aminoacid, benzoyl, acyl, thioaryl, polyethylene glycol based, ester linked, polyalkylene oxide, dextran, polyvinyl alcohols, carbohydrate based polymers, oligopeptide, polyglutamic acid, polyamino acid, onium salts of 2-halogenated aza-arenes, highly polar amino sugar, and the like. Suitable positions in the taxane molecule of the present invention for prodrug formation include but are not limited to the C2' and C7 position. Various forms of prodrugs are well known in the art. For examples of such prodrug derivatives, see: (a) *Design of Prodrugs*, edited by H. Bundgaard, (Elsevier, 1985) and *Methods in Enzymology*, Vol. 42, p. 309-396, edited by K. Widder, et al. (Acamedic Press, 1985); (b) *A Textbook of Drug Design and Development*, edited by Krosgaard-Larsen and H. Bundgaard, Chapter 5, "Design and Application of Prodrugs," by H. Bundgaard, p. 113-191 (1991); (c) H. Bundgaard, *Advanced Drug Delivery Reviews*, 8, 1-38 (1992); (d) H. Bundgaard, et al., *Journal of Pharmaceutical Sciences*, 77, 285 (1988); and (e) N. Kakeya, et al., *Chem Phar Bull*, 32, 692 (1984).

The taxanes of the instant invention are useful for inhibiting tumor growth in mammals including humans and are preferably administered in the form of a pharmaceutical composition comprising an effective antitumor amount of the compound of the instant invention in combination with at least one pharmaceutically or pharmacologically acceptable carrier. The carrier, also known in the art as an excepient, vehicle, auxiliary, adjuvant, or diluent, is any substance which is pharmaceutically inert, confers a suitable consistency or form to the composition, and does not diminish the therapeutic efficacy of the antitumor compounds. The carrier is "pharmaceutically or pharmacologically acceptable" if it does not produce an adverse, allergic or other untoward reaction when administered to a mammal or human, as appropriate.

The pharmaceutical compositions containing the antitumor compound of the present invention may be formulated in any conventional manner. Proper formulation is dependent upon the route of administration chosen. The compositions of the invention can be formulated for any route of administration so long as the target tissue is available via that route. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular antitumor compound used, and its concentration, stability and intended bioavailability; the disease, disorder or condition being treated with the composition; the subject, its age, size and general condition; and the route of administration. Suitable carriers are readily determined by one of ordinary skill in the art (see, for example, J. G. Nairn, in: *Remington's Pharmaceutical Science* (A. Gennaro, ed.), Mack Publishing Co., Easton, Pa., (1985), pp. 1492-1517, the contents of which are incorporated herein by reference).

The compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 *Modern Pharmaceutics*, Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

The compositions of the invention for oral administration comprise an effective antitumor amount of the compound of the invention in a pharmaceutically acceptable carrier. Suitable carriers for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, tragacanth, microcrystalline cellulose, colloidal silicon dioxide, croscarmellose sodium, talc, magnesium stearate, and stearic acid. Further, such solid dosage forms may be uncoated or may be coated by known techniques; e.g., to delay disintegration and absorption.

The antitumor compounds of the present invention may be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective antitumor amount of the antitumor compound in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art.

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid.

Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide_amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly (ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.,)(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia 24, The National Formulary 19*, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Preferred solvents include those known to stabilize the antitumor compounds, such as oils rich in triglycerides, for example, safflower oil, soybean oil or mixtures thereof, and alkyleneoxy modified fatty acid esters such as polyoxyl 40 hydrogenated castor oil and polyoxyethylated castor oils (e.g., Cremophor® EL solution or Cremophor® RH 40 solution). Commercially available triglyceride-rich oils include Intralipid® emulsified soybean oil (Kabi-Pharmacia Inc., Stockholm, Sweden), Nutralipid® emulsion (McGaw, Irvine, Calif.), Liposyn® II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), Liposyn® III 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels between 25% and 100% by weight based on the total fatty acid content (Dhasco® (from Martek Biosciences Corp., Columbia, Md.), DHA Maguro® (from Daito Enterprises, Los Angeles, Calif.), Soyacal®, and Travemulsion®. Ethanol is a preferred solvent for use in dissolving the antitumor compound to form solutions, emulsions, and the like.

Additional minor components can be included in the compositions of the invention for a variety of purposes well known in the pharmaceutical industry. These components will for the most part impart properties which enhance retention of the antitumor compound at the site of administration, protect the stability of the composition, control the pH, facilitate processing of the antitumor compound into pharmaceutical formulations, and the like. Preferably, each of these components is individually present in less than about 15 weight % of the total composition, more preferably less than about 5 weight %, and most preferably less than about 0.5 weight % of the total composition. Some components, such as fillers or diluents, can constitute up to 90 wt. % of the total composition, as is well known in the formulation art. Such additives include cryoprotective agents for preventing reprecipitation of the taxane, surface active, wetting or emulsifying agents (e.g., lecithin, polysorbate-80, pluronic 60, polyoxyethylene stearate, and polyethoxylated caster oils), preservatives (e.g., ethyl-p-hydroxybenzoate), microbial preservatives (e.g., benzyl alcohol, phenol, m-cresol, chlorobutanol, sorbic acid, thimerosal and paraben), agents for adjusting pH or buffering agents (e.g., acids, bases, sodium acetate, sorbitan monolaurate), agents for adjusting osmolarity (e.g., glycerin), thickeners (e.g., aluminum monostearate, stearic acid, cetyl alcohol, stearyl alcohol, guar gum, methyl cellulose, hydroxypropylcellulose, tristearin, cetyl wax esters, polyethylene glycol), colorants, dyes, flow aids, non-volatile silicones (e.g., cyclomethicone), clays (e.g., bentonites), adhesives, bulking agents, flavorings, sweeteners, adsorbents, fillers (e.g., sugars such as lactose, sucrose, mannitol, or sorbitol, cellulose, or calcium phosphate), diluents (e.g., water, saline, electrolyte solutions), binders (e.g., starches such as maize starch, wheat starch, rice starch, or potato starch, gelatin, gum tragacanth, methyl cellulose, hydroxypropyl methylcellulose, sodium carboxymethyl cellulose, polyvinylpyrrolidone, sugars, polymers, acacia), disintegrating agents (e.g., starches such as maize starch, wheat starch, rice starch, potato starch, or carboxymethyl starch, crosslinked polyvinyl pyrrolidone, agar, alginic acid or a salt thereof such as sodium alginate, croscarmellose sodium or crospovidone), lubricants (e.g., silica, talc, stearic acid or salts thereof such as magnesium stearate, or polyethylene glycol), coating agents (e.g., concentrated sugar solutions including gum arabic, talc, polyvinyl pyrrolidone, carbopol gel, polyethylene glycol, or titanium dioxide), and antioxidants (e.g., sodium metabisulfite, sodium bisulfite, sodium sulfite, dextrose, phenols, and thiophenols).

Dosage form administration by these routes may be continuous or intermittent, depending, for example, upon the patient's physiological condition, whether the purpose of the administration is therapeutic or prophylactic, and other factors known to and assessable by a skilled practitioner.

Dosage and regimens for the administration of the pharmaceutical compositions of the invention can be readily determined by those with ordinary skill in treating cancer. It is understood that the dosage of the antitumor compounds will be dependent upon the age, sex, health, and weight of the recipient, kind of concurrent treatment, if any, frequency of treatment, and the nature of the effect desired. For any mode of administration, the actual amount of antitumor compound delivered, as well as the dosing schedule necessary to achieve the advantageous effects described herein, will also depend, in part, on such factors as the bioavailability of the antitumor compound, the disorder being treated, the desired therapeutic dose, and other factors that will be apparent to those of skill in the art. The dose administered to an animal, particularly a human, in the context of the present invention should be sufficient to affect the desired therapeutic response in the animal over a reasonable period of time. Preferably, an effective amount of the antitumor compound, whether administered orally or by another route, is any amount which would result in a desired therapeutic response when administered by that route. Preferably, the compositions for oral administration are prepared in such a way that a single dose in one or more oral preparations contains at least 20 mg of the antitumor compound per $m^2$ of patient body surface area, or at least 50, 100, 150, 200, 300, 400, or 500 mg of the antitumor compound per $m^2$ of patient body surface area, wherein the average body surface area for a human is 1.8 $m^2$. Preferably, a single dose of a composition for oral administration contains from about 20 to about 600 mg of the antitumor compound per $m^2$ of patient body surface area, more preferably from about 25 to about 400 mg/$m^2$, even more preferably, from about 40 to about 300 mg/$m^2$, and even more preferably from about 50 to about 200 mg/$m^2$. Preferably, the compositions for parenteral administration are prepared in such a way that a single dose contains at least 20 mg of the antitumor compound per $m^2$ of patient body surface area, or at least 40, 50, 100, 150, 200, 300, 400, or 500 mg of the antitumor compound per $m^2$ of patient body surface area. Preferably, a single dose in one or more parenteral preparations contains from about 20 to about 500 mg of the antitumor compound per $m^2$ of patient body surface area, more preferably from about 40 to about 400 mg/$m^2$, and even more preferably, from about 60 to about 350 mg/$m^2$. However, the dosage may vary depending on the dosing schedule which can be adjusted as necessary to achieve the desired therapeutic effect. It should be noted that the ranges of effective doses provided herein are not intended to limit the invention and represent preferred dose ranges. The most preferred dosage will be tailored to the individual subject, as is understood and determinable by one of ordinary skill in the art without undue experimentation.

The concentration of the antitumor compound in a liquid pharmaceutical composition is preferably between about 0.01 mg and about 10 mg/mL of the composition, more preferably between about 0.1 mg and about 7 mg/mL, even more preferably between about 0.5 mg and about 5 mg/mL, and most preferably between about 1.5 mg and about 4 mg per ml. In one embodiment, the concentration of 9091 in this formulation is 2 to 4 mg/mL. Relatively low concentrations are generally preferred because the antitumor compound is most soluble in the solution at low concentrations. The concentration of the antitumor compound in a solid pharmaceutical composition for oral administration is preferably between about 5 weight % and about 50 weight %, based on the total weight of the composition, more preferably between about 8 weight % and about 40 weight %, and most preferably between about 10 weight % and about 30 weight %.

In one embodiment, solutions for oral administration are prepared by dissolving an antitumor compound in any pharmaceutically acceptable solvent capable of dissolving the compound (e.g., ethanol or polyethylene glycol) to form a solution. An appropriate volume of a carrier which is a surfactant, such as Cremophor® EL solution, polysorbate 80, Solutol HS15, or Vitamin E TPGS, is added to the solution while stirring to form a pharmaceutically acceptable solution for oral administration to a patient. For example, the resulting compositions, may contain up to about 15% ethanol and/or up to about 15% surfactant, more typically, the concentrations will be about 7.5-15% by volume ethanol with an equal volume of surfactant and distilled water in the range of 75-90% by volume. For taste purposes, a fraction of the distilled water can be replaced by a diluted cherry or raspberry syrup, preferably, about 10-30% syrup with the remainder water. In one embodiment, the concentration of 9091 in this formulation is 2 to 4 mg/mL. If desired, such solutions can be formulated to contain a minimal amount of, or to be free of, ethanol, which is known in the art to cause adverse physiological effects when administered at certain concentrations in oral formulations. In a preferred embodiment, the solution comprises about 10% ethanol, about 10% surfactant selected from polysorbate 80 (e.g., Tween 80®), polyethoxylated castor oils (e.g., Cremophor®), and mixtures thereof, and about 90% distilled water.

In another embodiment, powders or tablets for oral administration are prepared by dissolving an antitumor compound in any pharmaceutically acceptable solvent capable of dissolving the compound (e.g., ethanol or polyethylene glycol) to form a solution. The solvent can optionally be capable of evaporating when the solution is dried under vacuum. An additional carrier can be added to the solution prior to drying, such as Cremophor® EL solution. The resulting solution is dried under vacuum to form a glass. The glass is then mixed with a binder to form a powder. The powder can be mixed with fillers or other conventional tabletting agents and processed to form a tablet for oral administration to a patient. The powder can also be added to any liquid carrier as described above to form a solution, emulsion, suspension or the like for oral administration.

Emulsions for parenteral administration can be prepared by dissolving an antitumor compound in any pharmaceutically acceptable solvent capable of dissolving the compound (e.g., ethanol or polyethylene glycol) to form a solution. An appropriate volume of a carrier which is a fat emulsion, such as Liposyn® II, Liposyn® III, or Intralipid® emulsion, is added to the solution while stirring to form a pharmaceutically acceptable emulsion for parenteral administration to a patient. For example, the resulting composition may contain up to about 10% ethanol and/or more than about 90% carrier, more typically, the concentration will be about 5-10% by volume ethanol and about 90-95% by volume carrier. In one embodiment, the concentration of 3102 in the dosing solution is about 1-2 mg/mL. If desired, such emulsion can be formulated to contains a minimum amount of, or to be free of ethanol or Cremophor® solution, which are known in the art to cause adverse physiological effects when administered at certain concentrations in parenteral formulations. In a preferred embodiment, the emulsion comprises about 5% ethanol and about 95% (e.g., Intralipid 20%, Liposyn II 20%, or a mixture thereof). In this preferred embodiment, the resulting composition is free of agents which are known to cause adverse physiological effects, such as polyethoxylated castor oils (e.g., Cremophor®) and polysorbate 80 (e.g., Tween 80®).

Solutions for parenteral administration can be prepared by dissolving an antitumor compound in any pharmaceutically acceptable solvent capable of dissolving the compound (e.g., ethanol or polyethylene glycol) to form a solution. An appropriate volume of a carrier which is a surfactant, such as Cremophor® solution, polysorbate 80, or Solutol HS15, is added to the solution while stirring to form a pharmaceutically acceptable solution for parenteral administration to a patient. For example, the resulting composition may contain up to about 10% ethanol and/or up to about 10% surfactant, more typically, the concentration will be about 5-10% by volume ethanol with an equal volume of surfactant and saline in the range of 80-90% by volume. If desired, such solutions can be formulated to contain a minimal amount of, or to be free of, ethanol or Cremophor® solution, which are known in the art to cause adverse physiological effects when administered at certain concentrations in parenteral formulations. In a preferred embodiment, the solution comprises about 5% ethanol, about 5% polysorbate 80 (e.g., Tween 80®) or polyethoxylated castor oils (e.g., Cremophor®), and about 90% saline (0.9% sodium chloride). To minimize or eliminate potential adverse effects (e.g., hypersensitivity reactions), a patient receiving this embodiment is preferably pretreated with dexamethasone, diphenhydramine, or any other agent known in the art to minimize or eliminate these adverse reactions.

Other suitable parenteral formulations include liposomes. Liposomes are generally spherical or spheroidal clusters or aggregates of amphiphatic compounds, including lipid compouds, typically in the form of one or more concentric layers, for example monolayers or bilayers. The liposomes may be formulated from either ionic or nonionic lipids. Liposomes from nonionic lipids are also referred to as niosomes. References for liposomes include: (a) *Liposomes Second Edition: A Practical Approach*, edited by V. Torchillin and V. Weissig, Oxford University Press, 2003; (b) M. Malmstein, *Surfactants and Polymers in Drug Delivery*, Marcel Dekker Inc., 2002; and (c) Muller et al., *Emulsions and Nanosuspensions for the Formulation of Poorly Soluble Drugs*, Medpharm Scientific Publishers, 1998.

If desired, the emulsions or solutions described above for oral or parenteral administration can be packaged in IV bags, vials or other conventional containers in concentrated form and diluted with any pharmaceutically acceptable liquid, such as saline, to form an acceptable taxane concentration prior to use as is known in the art.

The terms "hydroxyl protecting group" and "hydroxy protecting group" as used herein denote a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in *Protective Groups in Organic Synthesis* by T. W. Greene, John Wiley and Sons, 1981, or Fieser & Fieser. Exemplary hydroxyl protecting groups include methoxymethyl, 1-ethoxyethyl, benzyloxymethyl, (β-trimethylsilylethoxy) methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

As used herein, "Ac" means acetyl; "Bz" means benzoyl; "TES" means triethylsilyl; "TMS" means trimethylsilyl; "LAH" means lithium aluminum hydride; "10-DAB" means 10-desacetylbaccatin III"; "THF" means tetrahydrofuran; "DMAP" means 4-dimethylamino pyridine; "LHMDS" means lithium hexamethyldisilazanide; "TESCl" means triethylsilyl chloride; "cPtc-Cl" means cyclopentanecarbonyl chloride; "DMF" means N,N-dimethylformamid; "MOP" means 2-methoxypropene; "iProc" means N-isopropoxycarbonyl; "iProc-Cl" means isopropyl chloroformate; and "LDA" means lithium diisopropylamide.

The following examples illustrate the invention.

EXAMPLE 1

Preparation of Compound 9091

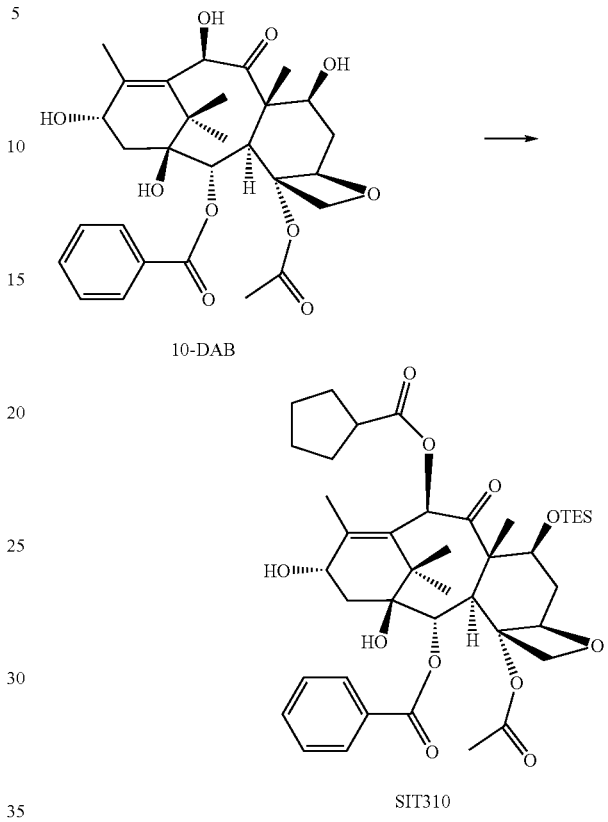

Protection and Acylation of 10-DAB to SIT310. Using the following procedure, tandem protection of 10-DAB's C7-hydroxyl with triethylsilyl chloride (TESCI) and acylation of its $C_{10}$-hydroxyl with cyclopentanecarbonyl chloride (cPtc-CI) produced SIT310.

Preferably, the reaction is carried out at 6 mL of DMF per 1 g of 10-DAB as a clear solution (10-DAB is soluble in DMF at ~5 mL/g at 22° C., but will precipitate when cooling to 0-5° C.). Addition of DMAP to the solution of 10-DAB in DMF at room temperature will aid its solubility. Preferably, the anhydrous solvents and reactors are under inert nitrogen atmosphere. Water will consume triethylsilyl chloride with a molar 1:2 ratio.

To an oven dried 1-L jacketed 3-neck round bottom flask (RBF) equipped with magnetic stirring, internal temperature probe and an addition funnel under an inert nitrogen atmosphere was placed 10-DAB (54.46 g, 0.100 mol), DMAP (36.60 g, 0.300 mol) and anhydrous DMF (330 mL). The mixture (0.3 M) was stirred to give a clear light yellow solution at 22° C. The reaction mixture was cooled to an internal reactor temperature of 0-5° C. with a circulating chiller.

7-TES Protection: The addition funnel was charged with TESCI (17.6 mL, 0.105 mol, 1.05 eq). When the internal reactor temperature was <5° C., drop-wise addition of the TESCI was initiated to control the exotherm and maintain the internal reactor temperature <5° C. (20-30 min addition time). After addition of 15 mL of TESCI, DMAP-HCl salt began to precipitate. After the addition was complete, the reaction was stirred at 0 to 5° C. for 2.5 h. TLC monitoring (3:1, EtOAc:Heptanes) showed a small amount of starting material (Rf=0.20) compared to the 7-TES-10-DAB product (Rf=0.65). HNMR sampling of the reaction mixture showed the amount of starting material was 2.5% of the product according to the integrals of the C10 carbinol proton resonances. Additional TESCl (0.45 mL, 0.0027 mol) was added and the mixture was stirred at 0 to 5° C. After 2 h, HNMR sampling showed <1% of the starting 10-DAB approximately 1.2% of the 7,13-bisilylated side product (the reaction was stirred overnight without further changes).

10-cPtc Formation: The addition funnel was charged with cyclopentanecarbonyl chloride (12.76 mL, 0.105 mol) and added drop-wise to the reaction flask over 30 min to control the exotherm and maintain the internal reactor temperature <10° C. After the addition was complete, the mixture was stirred at 15-22° C. over 12 h. TLC monitoring of the reaction mixture showed approximately 95% conversion to the less polar product. HNMR sampling of the reaction mixture showed 4.5% of the intermediate 7-TES-10-DAB remained relative to the product according to the integrals of the C10 carbinol proton resonances. Additional cPtc-Cl (0.55 mL, 0.0045 mol) was added and the mixture stirred for 4.5 h. TLC monitoring (1:1, EtOAc:Heptanes) showed complete conversion to the product and work-up was initiated.

Work-up: The reaction mixture was gradually poured into a rapidly stirring 3-L flask containing 1.5 L of ice-cold water over 5 min to form a thick white precipitate. After stirring for 15 min, the precipitate was collected by vacuum filtration through a medium frit Buchner funnel. The filtered cake was washed thoroughly with pure water. The water filtrate showed no product by TLC and was discarded. The filtered cake was dissolved in ethyl acetate (300 mL) and collected into the vacuum filtration flask. The funnel was washed with ethyl acetate (100 mL) into the ethyl acetate filtrate. The filtrate was transferred into a 2-L separatory funnel and washed with water (1×100 mL), saturated sodium bicarbonate solution (1×100 mL) and brine (1×50 mL). The organic layer was dried over $MgSO_4$ (30 g) for 1 h. The $MgSO_4$ was filtered off and washed with ethyl acetate into the filtrate. The filtrate was concentrated under rotary evaporation at 40° C. to ~100 mL. The remaining ethyl acetate was exchanged with acetonitrile (500 mL). The mixture was further concentrated until crystal formation was observed about 375 ml of acetonitrile remained in the evaporating flask. The concentration was stopped and 50 mL of acetonitrile was added to aid the agitation of the crystals. The solution then was cooled to −20° C. for 1 h while rotating on the rotovap. The crystals were collected by vacuum filtration. The filtered cake was washed with −20° C. cold acetonitrile (150 mL) and ambient temperature heptanes (200 mL). The crystals were dried under high vacuum (<0.1 mmHg) at 22° C. overnight to constant weight (59.90 g, 79.3%). Mp: 241-243° C., 97.5% HPLC purity. KF: 0.96% w/w water. HNMR spectrum of the crystals conformed to the structure of SIT310. $[\alpha]_D^{20}$=−43.5 (MeOH, 2.07).

The acetonitrile filtrate was concentrated under rotary evaporation to ~100 mL to induce a 2nd crop of crystals.

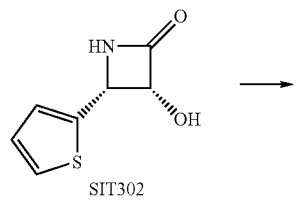
SIT302

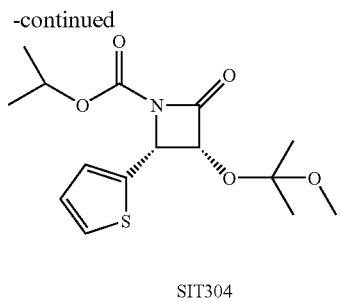
SIT304

Tandem Protection and N-Acylation-Conversion of SIT302 to SIT304. Using the following procedure, tandem protection of SIT302's hydroxyl with 2-methoxypropene (MOP) and introduction of the N-isopropoxycarbonyl (iProc) group using isopropyl chloroformate (iProc-Cl) gave SIT304.

Preferably, the following reactions take place under anhydrous conditions and solvents under nitrogen inert atmospheres. Glassware and equipments should be triethylamine base washed and dried thoroughly. MOP polymerized readily in the presence of trace levels of acid at temperatures >0° C. SIT302 will precipitate at −25° C. at a concentration of <15 mL THF/g.

MOP Protections: To a dried 2-L RBF with magnetic stirring under nitrogen equipped with a 0.5-L addition funnel and a low temperature probe was charged SIT302 (36.0 g, 0.213 mol) and THF (540 mL) to give a clear light yellow solution. The solution was cooled to −25° C. then charged with pTsOH monohydrate (1.8 g, 9.4 mmol). The addition funnel was charged with MOP (23.5 mL, 0.245 mol). After the reactor temperature reached −25° C., drop-wise addition of the MOP at a rate to control the exotherm and maintain the reactor temperature <−20° C. (15 min). After the addition was complete, TLC monitoring eluting with 2:1 ethyl acetate:hexanes showed ~15% SIT302 (Rf=0.2) remained. Additional MOP (5 mL, 0.052 mol) was added drop-wise over 5 min to complete the conversion to the less polar MOP protected SIT302 (Rf=0.5). The ketal forming reaction was quenched with triethylamine (108 mL, 0.775 mol) at −25° C.

N-Acylation: After the MOP protection reaction was quenched, DMAP (3.24 g, 0.0265 mol) was added to the reaction flask and warmed to ambient temperature. The addition funnel was dried under nitrogen stream and charged with iProc-Cl (245 mL, 1.0 M in toluene, 0.245 mol). After the reactor temperature was at 22° C., drop-wise addition of the chloroformate was initiated to control the exotherm and maintain the reactor temperature below 28° C. The addition was complete in 30 min to give a white triethylammonium chloride precipitate. After stirring at ambient temperature for 1 h, TLC monitoring eluting with 1:1 ethyl acetate:heptanes showed ~90% conversion and 10% of the MOP-SIT302 remained. Additional iProc-Cl (40 mL, 0.04 mol) was added to the reaction. After stirring for 2.5 h at 22° C., TLC showed complete conversion to the less polar product and work-up was initiated.

Work-up: To the reaction mixture was added a 1:1 mixture of saturated sodium bicarbonate:brine (300 mL) and vigorously stirred for 10 min. The mixture was then transferred to a 2-L separatory funnel and the layers were allowed to separate. The lower aqueous layer was drained and discarded. The organic layer was washed twice with brine (2×100 mL) and dried over $MgSO_4$ (15 g) over 1 h with agitation. The $MgSO_4$ was filtered off and the filtered cake was washed with ethyl acetate to ensure complete recovery of the product (TLC).

The filtrate was transferred to 3-L evaporating and concentrated under vacuum rotary evaporation at 40° C. to an oil to remove the toluene and THF solvents. The viscous oil was dissolved in ethyl acetate (500 mL) in the evaporating flask of the rotary evaporator and heptanes (1500 mL) was added to the evaporating flask over 10 min with good agitation. The clear solution was further concentrated under vacuum. After approximately 350 mL of the solvent mixture had been removed, crystal formation began and vacuum concentration was stopped. The mixture was cooled with continued rotation for 1 h at 22° C., then 1 h at 0° C. The crystals were collected by vacuum filtration and the filtered cake was washed with cold heptanes (150 mL). The product was dried under high vacuum (0.1 mmHg) at ambient temperature to constant weight (51.52 g, 0.157 mol, 73.7%). The filtrate was concentrated to approximately 200 mL of volume to induce crystallization of the 2nd crop. After cooling to 0° C. for 1 h, the 2nd crop was collected by vacuum filtration and washed with heptanes (~50 mL) and dried to constant weight (10.25 g, 0.031 mol, 14.7%). After TLC monitoring of the two crops showing similar in purity they were combined (61.52 g, 88.4%). Mp: 74-75° C., 99.4% HPLC purity. KF: 1.48% w/w water. HNMR spectrum of the crystals conformed to the structure of SIT304. $[\alpha]_D^{20}$=+3.6 (MeOH, 0.93). It was stored in triethylamine base washed flask under nitrogen at <−20° C.

−45° C. and a solution of freshly titrated n-BuLi (54 mL, 1.62 M, 85.83 mmol) was added drop-wise to control the exotherm and maintain the reactor temperature <−40° C. After the addition was completed over 30 min, the cooling bath was raised to 0-5° C. before use.

Coupling reaction: To an oven dried 1-L RBF under nitrogen equipped with magnetic stirring and internal temperature probe was charged SIT310 (54.0 g, 71.525 mmol), SIT304 (28.1 g, 85.83 mmol) and THF (325 mL, 0.22 M). The mixture was cooled to −45° C. The addition funnel was charged with the freshly prepared LDA and it was added drop-wise to the reaction flask over 30 min to control the exotherm and maintain the reactor temperature <−40° C. After the addition, the reactor temperature was raised to −20° C. and maintained while stirring for 1.5 h. TLC monitoring of the reaction (1:3/EtOAc:Hept) showed ~10% of SIT31 (Rf=0.25,) ~90% of the product SIT312 and none of the starting SIT304 remained. Additional SIT304 (2.8 g, 8.56 mmol) was added to the reaction mixture as a solid. After 1.5 h stirring at −20° C., the reaction was completed by TLC analysis and work-up was initiated.

Work-up: To the reaction flask at −20° C. was added a 1:1 mixture of saturated sodium bicarbonate and brine (100 mL) to quench the reaction. The reaction flask was warmed to ambient temperature and transferred to a separatory funnel. Ethyl acetate (200 mL) was added to aid the layers splitting.

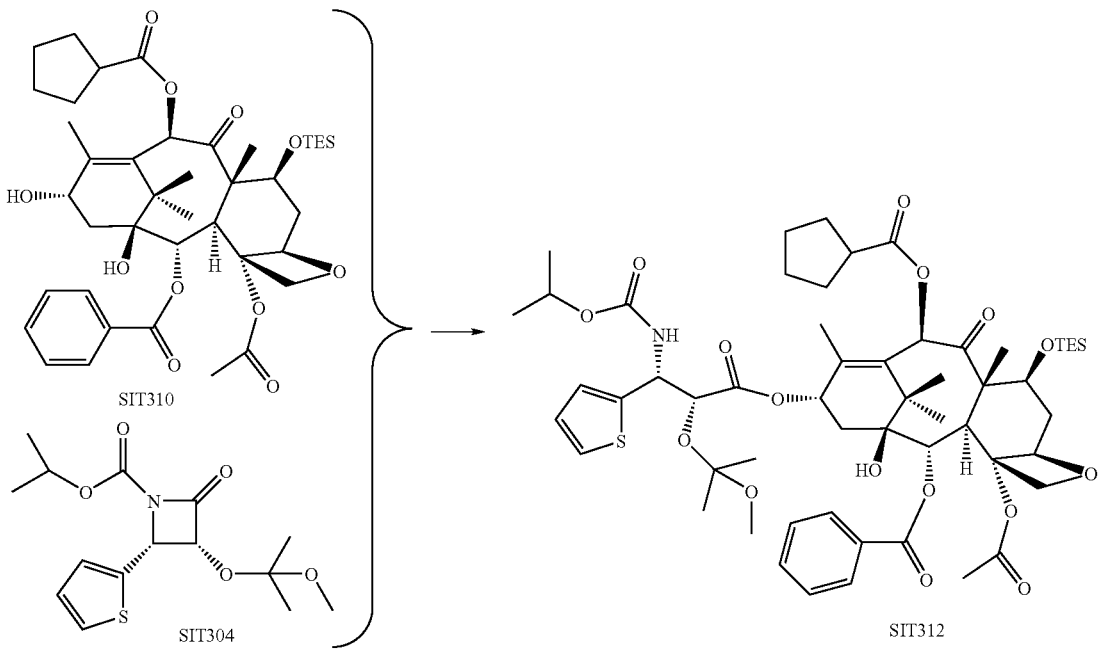

Lithium Alkoxide Coupling-Conversion of SIT310 to SIT312. Using the following procedure, SIT312 and SIT304 were coupled to produce SIT312.

Reactions are moisture sensitive. Preferably, the reactions are carried out under inert nitrogen atmosphere and anhydrous reactors and solvents. Lithium diisopropylamide (LDA) base should be freshly prepared before use.

LDA preparation: To an oven dried 250-mL RBF under nitrogen equipped with magnetic stirring and internal temperature probe was charged diisopropylamine (13.1 mL, 92.98 mmol) and THF (26 mL). The mixture was cooled to The aqueous phase was drained and discarded. The organic layer was washed once more with brine (50 mL) and dried over $MgSO_4$ (30 g). The $MgSO_4$ was filtered off and the filtered cake was washed with ethyl acetate (100 mL) into the filtrate. The filtrate was concentrated under vacuum rotary evaporation to approximately 150 mL in volume. The remaining solvent was exchanged with isopropanol (500 mL). After the further concentration to an approximate volume of 350-400 mL crystals formation began and concentration was stopped. The mixture was cooled to 0° C. with agitation for 1 h. The crystals were collected by vacuum filtration and washed with pre-cooled 0° C. isopropanol (200 mL) and dried to constant weight (73.58 g, 68.0 mmol, 95.0%) under high vacuum (0.1 mmHg). HNMR spectra of the crystals conformed to the structure of SIT312. MP: 137-140° C., HPLC purity 95.4%. It was unstable under HPLC preparation condition and loss of the 2'-MOP protection during anlysis (0.83%).

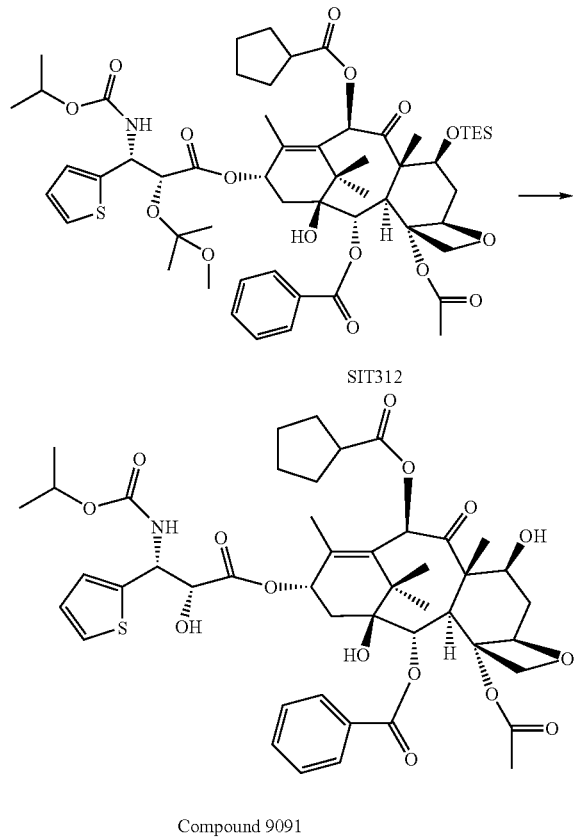

Compound 9091

Tandem Deprotection-Conversion of SIT312 to 9091. Using the following procedure, tandem removal of SIT312's MOP and TES protecting groups under acidic conditions produced 9091.

To a jacketed 1-L RBF equipped with magnetic stirring, internal temperature probe and an addition funnel was charged SIT312 (70.0 g, 64.67 mmol) and THF (350 mL, 0.185 M). The mixture was cooled to 0° C. with a circulating bath. The addition funnel was charged with formic acid (96%, 175 mL, 4.45 mol). The formic acid was added drop-wise over 30 min to control the exotherm and maintain the reactor temperature <10° C. After complete addition of the formic acid, the addition funnel was charged with 1.0 M HCl (87.5 mL, 87.5 mmol). Drop-wise addition of the HCl was carried out over 15 min to control the exotherm and maintain the reactor temperature <10° C. TLC of reaction mixture (1:1 EtOAc:Hept) after the addition showed loss of the MOP protecting group immediately to give a more polar product (Rf=0.65) compared to SIT312 (Rf=0.7). The mixture was stirred at 8 to 10° C. After 9 h, TLC showed >95% conversion to a more polar product along with approximately 2-3% byproduct (Rf=0.55) and ~1% the Rf=0.65 intermediate and work-up was initiated.

Work-up: The reaction was diluted with ethyl acetate (1 L) and transferred to a 3-L separatory funnel and washed twice with water (2×500 ml), twice with saturated sodium bicarbonate (2×100 mL). The pH of the organic layer was checked to be 8 and it was washed twice with brine (2×100 mL). Monitoring of the aqueous phase showed no product by TLC analysis. The organic layer was dried over $Na_2SO_4$ (100 g) for 1 h. The $Na_2SO_4$ was gravity filtered off with Whatman No. 1 filter paper and the filtered cake was washed with ethyl acetate to ensure complete recovery of the product. The filtrate was concentrated under vacuum rotary evaporation to give a foam (65.59 g). HNMR spectra of the foam confirmed the structure of 9091 along with triethylsilylated byproducts.

Recrystallization: The foam was dissolved in ethyl acetate (280 mL) and warmed to 50° C. with agitation. Heptanes (455 mL) was added gradually over 15 min to maintain a clear solution. The mixture was gradually cooled to ambient temperature. After 1 h at 22° C., seed crystals were introduced and crystal formation occurred within 5 min. The mixture was cooled in a 0° C. water bath for 1 h before the crystals were collected by vacuum filtration and the filtered cake was washed with a 0° C. cold mixture of 1:4 EtOAc:heptanes (200 mL). After drying at ambient temperature for 3 h and high vacuum (<0.1 mmHg), 57.23 g (57.23 g expected) of a white powder was obtained. HPLC analysis showed 96.8% purity and 1.2% of an impurity by area/area integration. The white powder was re-dissolved in ethyl acetate (225 mL) at 50° C. While agitating gently, heptanes (320 mL) was added gradually to maintain a clear solution. After the addition was complete, the mixture was cooled to 22° C. and crystal formation occurred spontaneously within 5 min. After 10 h at 22° C., the mixture was cooled to 0° C. After 1 h at 0° C., the crystals were collected by vacuum filtration and the filtered cake was washed with a 0° C. cold mixture of 1:4 EtOAc:heptanes (200 mL). HPLC analysis of the crystals showed 98.5% purity level. The white powder was dried at 50° C. and high vacuum (0.1 mmHg) for 2 days to a constant weight (40.58 g, 45.3 mmol, 70.0%). MP:159-161° C., 98.5% HPLC purity. $^1$HNMR and $^{13}$CNMR spectra conformed to the structure of 9091. $[\alpha]_D^{20}$=-43.1 (MeOH, 0.91).

The mother liquor from the first recrystallization was concentrated to give 15.0 g of a waxy material. It was triturated with heptanes (200 mL) to give approximately 7 g of a free flowing powder. The powder was purified by silica gel flash column chromatography eluting with 1:1 ethyl acetate:heptanes. Pooling the fractions containing 9091 and concentrating under vacuum rotary evaporation gave 5.84 g of 9091. Pooling the fractions containing the impurity gave 0.55 g of a white solid with a HNMR spectrum conforming to 7-formate-9091.

Concentration of the mother liquor from the 2nd recrystallization gave 4.50 g of material. It was combined with the 5.84 g of chromatographically purified 9091 of the 1st mother liquor to give a 10.34 g (17.8%).

| | | Compound 9091 $^1$H NMR data ($CDCl_3$) | | |
|---|---|---|---|---|
| | | 1H AND 13C CHEMICAL SHIFTS of Compound 9091 | | |
| No | Proton | ppm Pattern(J, Hz) | Carbon | ppm |
| 1 | H-10' | 1.10 d(6.19) | C19 | 9.541 |
| 2 | $CH_3$-16 | 1.15 s | C18 | 14.829 |
| 3 | H-11' | 1.16 d(6.19) | C10' | 21.833 |
| 4 | $CH_3$-17 | 1.26 s | C16' | 21.955 |
| 5 | 2H-24', 25' | 1.63 m | C20' | 22.581 |
| 6 | $CH_3$-19 | 1.68 s | C22' | 25.816 |
| 7 | OH-1 | 1.74 s | C11' | 25.877 |
| 8 | 2H-24', 25' | 1.76 m | C17 | 26.831 |
| 9 | $CH_3$-18 | 1.86 d(0.94) | C24', 25' | 29.593 |

-continued

Compound 9091 $^1$H NMR data (CDCl$_3$)
1H AND 13C CHEMICAL SHIFTS of Compound 9091

| No | Proton | ppm | Pattern(J, Hz) | Carbon | ppm |
|----|--------|------|----------------|--------|---------|
| 10 | H-6β | 1.89 | m | C23', 26' | 30.356 |
| 11 | 2H-23', 26' | 1.93 | m | C6 | 35.545 |
| 12 | 2H-23', 26' | 2.02 | m(6.64) | C15 | 43.206 |
| 13 | H-14α | 2.30 | ddd(15.30, 9.12) | C14 | 43.732 |
| 14 | CH$_3$-20' | 2.39 | s | C3 | 45.685 |
| 15 | H-6α | 2.54 | ddd(14.04, 9.57, 6.57) | C3' | 53.026 |
| 16 | H-14β | 2.56 | dd(15.30, 4.11) | C8 | 58.626 |
| 17 | H-22' | 2.92 | m(7.36, 6.85) | C9' | 69.057 |
| 18 | OH-2' | 3.44 | d(5.47) | C7 | 72.216 |
| 19 | H-3 | 3.83 | d(6.98) | C13 | 72.429 |
| 20 | H-20β | 4.18 | d(8.48) | C2' | 73.421 |
| 21 | H-20α | 4.31 | d(8.48) | C2 | 75.001 |
| 22 | H-7α | 4.42 | M(10.52, 4.29) | C10 | 75.176 |
| 23 | H-2' | 4.66 | dd(5.47, 2.24) | C20 | 76.481 |
| 24 | H-9' | 4.78 | bm(6.19) | C1 | 79.129 |
| 25 | H-5 | 4.95 | bd(9.57, 1.88) | C4 | 81.181 |
| 26 | H-N | 5.39 | d(9.47) | C5 | 84.462 |
| 27 | H-3' | 5.55 | dd(9.47, 2.24) | C7' | 125.460 |
| 28 | H-2 | 5.67 | d(6.98) | C5' | 125.544 |
| 29 | H-13β | 6.27 | ddd(9.12, 4.11, 0.94) | C6' | 127.039 |
| 30 | H-10α | 6.28 | s | C15', 17' | 128.664 |
| 31 | H-6' | 7.01 | dd(4.03, 5.13) | C13' | 129.115 |
| 32 | H-5' | 7.10 | dd(4.03, 1.15) | C14', 18' | 130.213 |
| 33 | H-7' | 7.29 | .dd(5.13, J:1.15) | C16' | 133.342 |
| 34 | 2H-15', 17' | 7.50 | dd(7.44, 7.12) | C11 | 133.655 |
| 35 | H-16' | 7.61 | dd,(7.44, 5.62) | C4' | 141.277 |
| 36 | 2H-18', 14' | 8.12 | d(8.59) | C12 | 141.804 |
| 37 | | | | C8' | 155.469 |
| 38 | | | | C12' | 167.067 |
| 39 | | | | C20' | 170.264 |
| 40 | | | | C1' | 172.187 |
| 41 | | | | C21' | 176.865 |
| 42 | | | | C9 | 203.746 |

EXAMPLE 2

In Vitro Cytotoxicity Measured by the Cell Colony Formation Assay

Four hundred cells (HCT 116 human colon carcinoma obtained from American Type Culture Collection, Manassas, Va.) were plated in 60 mm Petri dishes containing 2.7 mL of medium (modified McCoy's 5a medium containing 10% fetal bovine serum and 100 units/mL penicillin and 100 g/mL streptomycin). The cells were incubated in a CO$_2$ incubator at 37° C. for 5 h for attachment to the bottom of Petri dishes. The compound of the present invention was made up fresh in medium at ten times the final concentration, and then 0.3 mL of this stock solution was added to the 2.7 mL of medium in the dish. The cells were then incubated with drugs for 72 h at 37° C. At the end of incubation the drug-containing media were decanted, the dishes were rinsed with 4 mL of Hank's Balance Salt Solution (HBSS), 5 mL of fresh medium was added, and the dishes were returned to the incubator for colony formation. The cell colonies were counted using a colony counter after incubation for 7 days. Cell survival was calculated and the values of IC$_{50}$ (the drug concentration producing 50% inhibition of colony formation) were determined for each tested compound.

Identical assessments were carried out using VM46 (resistant variant of human colon carcinoma HCT 116 obtained from Dr. Li-Xi, M.D, Ph.D., California Pacific Medical Center, CA). DLD-1 (resistant human colon carcinoma obtained from American Type Culture Collection, Manassas, Va.) assessments were conducted in a similar manner using an MTT (3-(4,5-dimethylthiazol-2-yl)-2,5-diphenylterazolium bromide) assay.

| Compound | IN VITRO IC$_{50}$ (nM) HCT116 | IN VITRO IC$_{50}$ (nM) VM46 | IN VITRO IC$_{50}$ (nM) MTT:DLD-1 |
|----------|-------------------------------|------------------------------|-----------------------------------|
| paclitaxel | 2.1 | 20.0 | 10.1 |
| docetaxel | 0.6 | 6.7 | 9.1 |
| 9091 | 0.6 | 1.9 | 1.5 |

EXAMPLE 3

Oral Efficacy Evaluation of 9091

The efficacy of 9091 was evaluated in the human pancreatic tumor xenograft Panc-1, obtained from American Type Culture Collection, Manassas, Va. The tumor used for this study was maintained in athymic nude mice. A tumor fragment (1 mm$^3$) was implanted s.c. into the right flank of each test mouse. Tumors were monitored twice weekly and then daily as their volume approached 200-400 mm$^3$ with a mean of 250-300 mm$^3$. On Day 1 of the study, the animals were sorted into treatment groups with tumor sizes of 171.5-320.0 mm$^3$ and group mean tumor sizes of 212.6-216.0 mm$^3$. Tumor size, in mm$^3$, was calculated from the following formula:

$$\text{Tumor Volume} = \frac{w^2 \times l}{2}$$

where w=width and l=length in mm of the tumor. Tumor weight was estimated with the assumption that 1 mg is equivalent to 1 mm$^3$ of tumor volume. Mice were sorted into groups with six mice per group, and treated in accordance with the protocol in Tables 1A and 1B. All treatments were administered orally, once on Day 1 (qd×1). Groups 2 and 3 received compound 9091 at 120 and 60 mg/kg, respectively. In all groups, the dosing volume of 0.6 mL/20 g mouse was scaled to the body weight of each animal. Each animal was euthanized when its neoplasm reached the predetermined endpoint size (1200 mm$^3$). The time to endpoint (TTE) for each mouse was calculated by the following equation:

$$TTE = \frac{\log_{10}(\text{endpoint volume}) - b}{m}$$

where TTE is expressed in days, endpoint volume is in mm$^3$, b is the intercept, and m is the slope of the line obtained by linear regression of a log-transformed tumor growth data set. The data set is comprised of the first observation that exceeded the study endpoint volume and the three consecutive observations that immediately preceded the attainment of the endpoint volume. Animals that do not reach the endpoint are assigned a TTE value equal to the last day of the study (59 days). Animals classified as TR (treatment-related) deaths or NTRM (non-treatment-related metastasis) deaths are assigned a TTE value equal to the day of death. Animals classified as NTR (non-treatment-related) deaths are excluded from TTE calculations. Treatment efficacy was determined from tumor growth delay (TGD), which is defined as the increase in the median TTE for a treatment group compared to the control group:

$$TGD = T - C,$$

expressed in days, or as a percentage of the median TTE of the control group:

$$\% \, TGD = \frac{T - C}{C} \times 100$$

where:
T=median TTE for a treatment group and
C=median TTE for control Group 1.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study. An animal with a CR response at the termination of a study is additionally classified as a long-term tumor-free survivor (LTTFS).

With respect to toxicity, the animals were weighed daily on Days 1-5, then twice weekly until the completion of the study. The mice were examined frequently for overt signs of any adverse, drug-related side effects. Acceptable toxicity for the maximum tolerated dose (MTD) of a cancer drug in mice is defined by the NCI as a group mean body-weight (BW) loss of less than 20% during the test, and not more than one toxic death among ten treated animals. The log rank test was employed to analyze the significance of the difference between the TTE values of a drug-treated group and the vehicle-treated control group. The log rank test analyzes the data for all animals except the NTR deaths. The two-tailed statistical analyses were conducted at P=0.05. The group median tumor growth curves show the median tumor volume (MTV) as a function of time. When an animal exited the study due to tumor size or TR death, the final tumor volume recorded for the animal was included with the data used to calculate the median volume at subsequent time points. If more than one death occurred in a treatment group, the tumor growth curve for that group was truncated at the time of the second death.

Groups 2 and 3 received compound 9091 at 120 and 60 mg/kg, respectively. Groups 2 and 3 both experienced 212% TGD and highly significant antitumor activity (P<0.001). The MTVs, for six mice in each group, were 56 and 148 mm$^3$, respectively. In Group 2, 9091 produced three PR responses and three LTTFS. In Group 3, 9091 produced five PR responses and one LTTFS. Compound 9091 produced 100% survival and six regression responses at both the 120 and 60 mg/kg dose: these treatments yielded three and one LTTFS, and caused 10.7% and 5.5% group mean BW losses, respectively.

The data is contained in the following Tables 1A and 1B:

Treatment Response Summary For the Panc-1 Study

TABLE 1A

| | | Treatment Regimen 1 | | | | | | |
|---|---|---|---|---|---|---|---|---|
| Group | n | Agent | mg/kg | Route | Schedule | Median TTE | T − C | % TGD |
| 1 | 6 | 5% EC in Saline | | po | qd × 1 | 18.9 | — | — |
| 2 | 6 | 9091 | 120 | po | qd × 1 | 59.0 | 40.1 | 212% |
| 3 | 6 | 9091 | 60 | po | qd × 1 | 59.0 | 40.1 | 212% |

TTE—time to endpoint (Days), 1200 mg
T − C—Difference between TTE (Days) of treated versus control group, %
TGD = [(T − C)/C]
n—number of mice
5% EC – 5% Ethanol + 5% Cremophor

TABLE 1B

| Group | Tumor Burden Median(n), Day 59 | No. of PR | No. of CR | No. of LTTES | Max % BW Loss; Day | No. of TR | No. of NTR |
|---|---|---|---|---|---|---|---|
| 1 | —(0) | 0 | 0 | 0 | — | 0 | 0 |
| 2 | 56(6) | 3 | 3 | 3 | −10.7%; Day 10 | 0 | 0 |
| 3 | 148(6) | 5 | 1 | 1 | −5.5%; Day 10 | 0 | 0 |

CR—Non-palpable tumor for three consecutive measurements during the study
PR—Tumor regression to <=50% of starting size for three consecutive measurements during the study
LTTES—Long Term Tumor Free Survivors, animals classified as CRs at the end of a study
Logrank test is equivalent to the Mantel-Haenszel test; ns = not significant, * - p < 0.05,  - p < 0.01, * - p < 0.001, compared to Group 1
TR—Treatment Related Death
NTR—Non Treatment Related Death

EXAMPLE 4

IV Efficacy Evaluation of 9091

The antitumor activity of 9091 was evaluated against the human pancreatic tumor xenograft Panc-1. Human Panc-1 pancreatic carcinomas were maintained in athymic nude mice. A tumor fragment (1 mm³) was implanted s.c. into the right flank of each test mouse. Tumors were monitored twice weekly and then daily as their size approached 200-400 mm³ with a mean of 250-300 mm³. On Day 1 of the study, the animals were sorted into groups of six mice, with tumor sizes of 171.5-486.0 mm³ and group mean tumor sizes of 269.7-275.0 mm³. Mice were sorted into groups containing six mice each, and treated according to the protocol in Tables 2A and 2B. All treatments were administered intravenously. Control Group 1 mice received the ethanol 5% and Liposyn II 95% vehicle, once on Day 1 (qd×1). Group 2 received 9091 at 20 mg/kg every other day×5. Group 3 received 9091 at 30 mg/kg q4d×4. Groups 4 and 5 received 9091 qd×1 at 120 and 60 mg/kg, respectively. Dosing volumes were 0.5 ml/20 g body weight for qd×1 dosing regimens and 0.3 mL/20 g body weight for the qod×5 or q4d×4 dosing schedules. Dosing volumes were scaled to the body weight of each animal. The vehicle was given to Group 1 mice in a single dose on Day 1 (qd×1). Tumors in five of the six vehicle-treated mice grew to the 1200-mm³ endpoint volume, with a median TTE of 15.8 days. No regression responses were recorded. The presence of one 56-day survivor indicates a potential background level of one somewhat unsatisfactory tumor engraftments per group.

Group 2 received 9091 at 20 mg/kg qod×5. Group 3 received 9091 at 30 mg/kg q4d×4. Groups 4 and 5 received 9091 qd×1 at 120 and 60 mg/kg, respectively. Five TR deaths were recorded in Group 2, which could not be evaluated for treatment efficacy. Two Group 4 mice died of NTR causes. Groups 3-5 each experienced 254% TGD. This result is highly significant in Groups 3 and 5 (P<0.01), and significant in Group 4 (P<0.05). No tumors reached the endpoint volume in Groups 3-5; the MTV for six mice was 40, 58, and 126 mm³, respectively. In Group 3, five PR responses and one LTTFS were recorded. In each of Groups 4 and 5, six PR responses were recorded. 9091 was most effective on the 30 mg/kg q4d×4 regimen. This treatment yielded five PR responses and one LTTFS, while causing ~13% maximum group mean BW loss. Single doses at 120 and 60 mg/kg each produced six PR responses, while causing ~8% and ~5% group mean BW loss, respectively. These three 9091 treatments each produced six end-of-study survivors with MTVs of 40, 58, and 126 mm³, respectively.

Table 2: Treatment Response Summary For the Panc-1 Study

TABLE 2A

Treatment Regimen 1

| Group | n | Agent | mg/kg | Route | Schedule | Median TTE | T − C | % TGD |
|---|---|---|---|---|---|---|---|---|
| 1 | 6 | Vehicle | | IV | qd × 1 | 15.8 | — | — |
| 2 | 6 | 9091 | 20 | IV | qod × 5 | 10.0 | — | — |
| 3 | 6 | 9091 | 30 | IV | q4d × 4 | 56.0 | 40.2 | 254% |
| 4 | 6 | 9091 | 120 | IV | qd × 1 | 56.0 | 40.2 | 254% |
| 5 | 6 | 9091 | 60 | IV | qd × 5 | 56.0 | 40.2 | 254% |

TTE—time to endpoint (Days), 1200 mg
T − C—Difference between TTE (Days) of treated versus control group, %
TGD = [(T − C)/C]
n—number of mice

TABLE 2B

| Group | Tumor Burden Median(n), Day 56 | No. of PR | No. of CR | No. of LTTES | Logrank Significance | Max % BW Loss; Day | No. of TR | No. of NTR |
|---|---|---|---|---|---|---|---|---|
| 1 | 320(1) | 0 | 0 | 0 | — | — | 0 | 0 |
| 2 | 108(1) | 1 | 0 | 0 | — | −15.7%; Day 10 | 5 | 0 |
| 3 | 40.25(6) | 5 | 1 | 1 | p < 0.01 | −13.2%; Day 17 | 0 | 0 |
| 4 | 57.5(6) | 6 | 0 | 0 | p < 0.05 | −7.8%; Day 7 | 0 | 2 |
| 5 | 126(6) | 6 | 0 | 0 | p < 0.01 | −4.9%; Day 7 | 0 | 0 |

CR—Non-palpable tumor for three consecutive measurements during the study
PR—Tumor regression to <=50% of starting size for three consecutive measurements during the study
LTTES—Long Term Tumor Free Survivors, animals classified as CRs at the end of a study
Logrank test is equivalent to the Mantel-Haenszel test; ns = not significant, * - p < 0.05,  - p < 0.01, * - p < 0.001, compared to Group 1
TR—Treatment Related Death
NTR—Non Treatment Related Death

EXAMPLE 5

Efficacy Study for 9091 in the HT29 Xenograft

Following similar oral and intravenous administration regimens as for the Panc-1 xenograft described in Examples 3 and 4, compound 9091 was also evaluated in the HT29 (human colon carcinoma obtained from American Type Culture Collection, Manassas, Va.) xenograft. The results are summarized in Tables 3 and 4.

TABLE 3A

Protocol Design For The HT29 Study Using Compound 9091

Treatment Regimen 1

| Group | n | Agent | mg/kg | Route | Schedule |
|---|---|---|---|---|---|
| 1 | 6 | 5% EC in Saline | | po | qd × 1 |
| 18 | 6 | 9091 | 15 | po | q4d × 4 |

TABLE 3A-continued

Protocol Design For The HT29 Study Using Compound 9091

Treatment Regimen 1

| Group | n | Agent | mg/kg | Route | Schedule |
|---|---|---|---|---|---|
| 19 | 6 | 9091 | 30 | po | q4d × 4 |
| 20 | 6 | 9091 | 45 | po | q4d × 4 |
| 21 | 6 | 9091 | 60 | po | q4d × 4 |

TABLE 3B

Treatment Response Summary For The HT29 Study Using Compound 9091

| Group | n | Agent | mg/kg | Route | Schedule | MDS to 1.0 g ±SEM (n) | Max. % BW Loss; Day | # Death[a] TR | # Death[a] NTR |
|---|---|---|---|---|---|---|---|---|---|
| 1 | 6 | 5% EC in Saline | | po | qd × 1 | 16.5 ± 1.5 (6) | — | 0 | 0 |
| 18 | 6 | 9091 | 15 | po | q4d × 4 | 24.4 ± 1.4 (6) | — | 0 | 0 |
| 19 | 6 | 9091 | 30 | po | q4d × 4 | 25.6 ± (1) | −11.3%; Day 21 | 0 | 0 |
| 20 | 6 | 9091 | 45 | po | q4d × 4 | ± (0) | −22.6%; Day 17 | 0 | 0 |
| 21 | 6 | 9091 | 60 | po | q4d × 4 | ± (0) | −28.1%; Day 17 | 4 | 0 | n—number of mice
5% EC—5% Ethanol and 5% cremophor

TABLE 4A

Protocol Design for The HT29 Study Using Compound 9091 (IV)

Treatment Regimen 1

| Group | n | Agent | mg/kg | Route | Schedule |
|---|---|---|---|---|---|
| 1 | 6 | No treatment | | | |
| 2 | 6 | vehicle | | IV | Q4d × 4 |
| 3 | 6 | vehicle | | IV | Q4d × 4 |
| 4 | 6 | vehicle | | IV | Q4d × 4 |
| 5 | 6 | 9091 | 120 | IV | QD × 1 |
| 6 | 6 | 9091 | 60 | IV | QD × 1 |
| 7 | 6 | 9091 | 120 | IV | QD × 1 |
| 8 | 6 | 9091 | 60 | IV | QD × 1 |
| 9 | 6 | 9091 | 120 | IV | QD × 1 |
| 10 | 6 | 9091 | 60 | IV | QD × 1 |
| 14 | 6 | 9091 | 30 | IV | Q4d × 4 |
| 15 | 6 | 9091 | 20 | IV | Q4d × 4 |
| 16 | 6 | 9091 | 30 | IV | Q4d × 4 |
| 17 | 6 | 9091 | 20 | IV | Q4d × 4 |
| 18 | 6 | 9091 | 30 | IV | Q4d × 4 |
| 19 | 6 | 9091 | 20 | IV | Q4D × 4 |

TABLE 4B

Treatment Response Summary for the HT29 Study Using Compound 9091

| Group | n | Regimen 1 Agent | mg/kg | Regimen 2 Agent | mg/kg | MDS to 1.0 g ±SEM(n) | Max. % BW Loss; Day | # Death[a] TR | # Death[a] NTR |
|---|---|---|---|---|---|---|---|---|---|
| 1 | 6 | No treatment | | | | 16.1 ± 3.0 (10) | — | 0 | 1 |
| 2 | 6 | vehicle | | 5% E-95% I-20 | 0.3 | 21.9 ± 4.0 | — | 0 | 0 |
| 3 | 6 | vehicle | | 5% ET in Saline | 0.3 | 18.4 ± 3.6 | — | 0 | 0 |
| 4 | 6 | vehicle | | 5% EC in Saline | 0.3 | 20.4 ± 2.9 | — | 0 | 0 |
| 5 | 6 | 9091 | 120 | 5% E-95% I-20 | 0.5 × 2 | ± | −11.8%; Day 10 | 0 | 0 |
| 6 | 6 | 9091 | 60 | 5% E-95% I-20 | 0.5 | 51.9 ± 0.0 | −8.9%; Day 7 | 0 | 0 |
| 7 | 6 | 9091 | 120 | 5% ET in Saline | 0.5 × 2 | ± | −23.7%; Day 10 | 5 | 0 |
| 8 | 6 | 9091 | 60 | 5% ET in Saline | 0.5 | 51.8 ± | −4.9%; Day 7 | 0 | 0 |
| 9 | 6 | 9091 | 120 | 5% EC in Saline | 0.5 × 2 | ± | −16.6%; Day 14 | 0 | 0 |
| 10 | 6 | 9091 | 60 | 5% EC in Saline | 0.5 | 46.0 ± | −8.2%; Day 10 | 0 | 0 |
| 14 | 6 | 9091 | 30 | 5% E-95% I-20 | 0.3 | ± | −15.6%; Day 17 | 0 | 0 |
| 15 | 6 | 9091 | 20 | 5% E-95% I-20 | 0.3 | ± | −17.8%; Day 17 | 0 | 0 |
| 16 | 6 | 9091 | 30 | 5% ET in Saline | 0.3 | ± | −18.3%; Day 17 | 0 | 0 |
| 17 | 6 | 9091 | 20 | 5% ET in Saline | 0.3 | ± | −14.4%; Day 14 | 0 | 0 |
| 18 | 6 | 9091 | 30 | 5% EC in Saline | 0.3 | ± | −22.7%; Day 21 | 0 | 0 |
| 19 | 6 | 9091 | 20 | 5% EC in Saline | 0.3 | ± | −9.9%; Day 14 | 0 | 0 |

[a] # Death: TR(Treatment Related); NTR(Non-Treatment Related)

Figure 2:
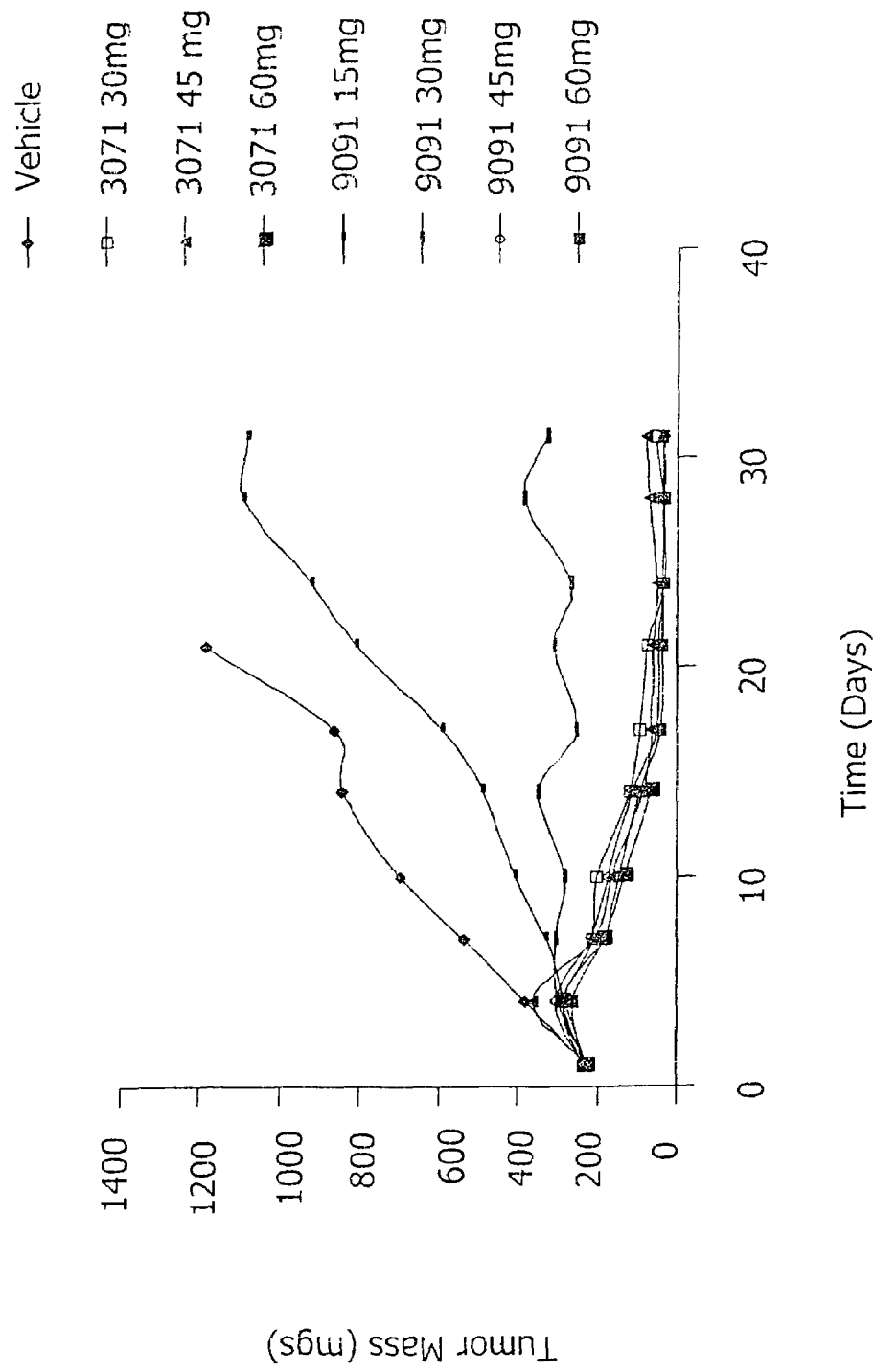
FIG. 2 depicts median tumor growth curves for mice treated with compound 9091 vs. compound 3071 in the HT29 study (oral q4d×4 doses).
Figure 3:
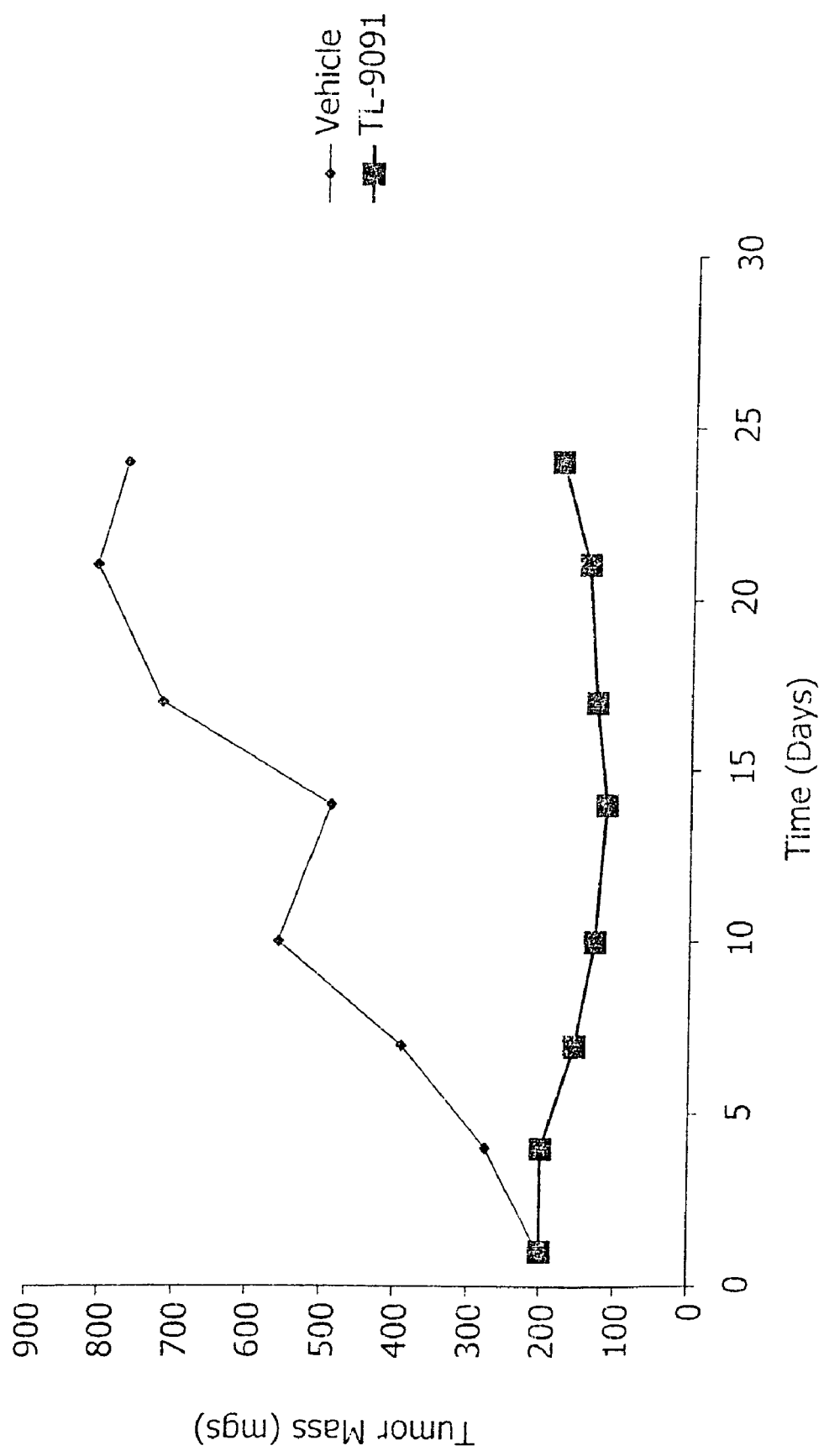
FIG. 3 depicts median tumor growth curves for mice treated with compound 9091 in the HT29 study (oral single doses of 60 mg/kg).
Figure 4:
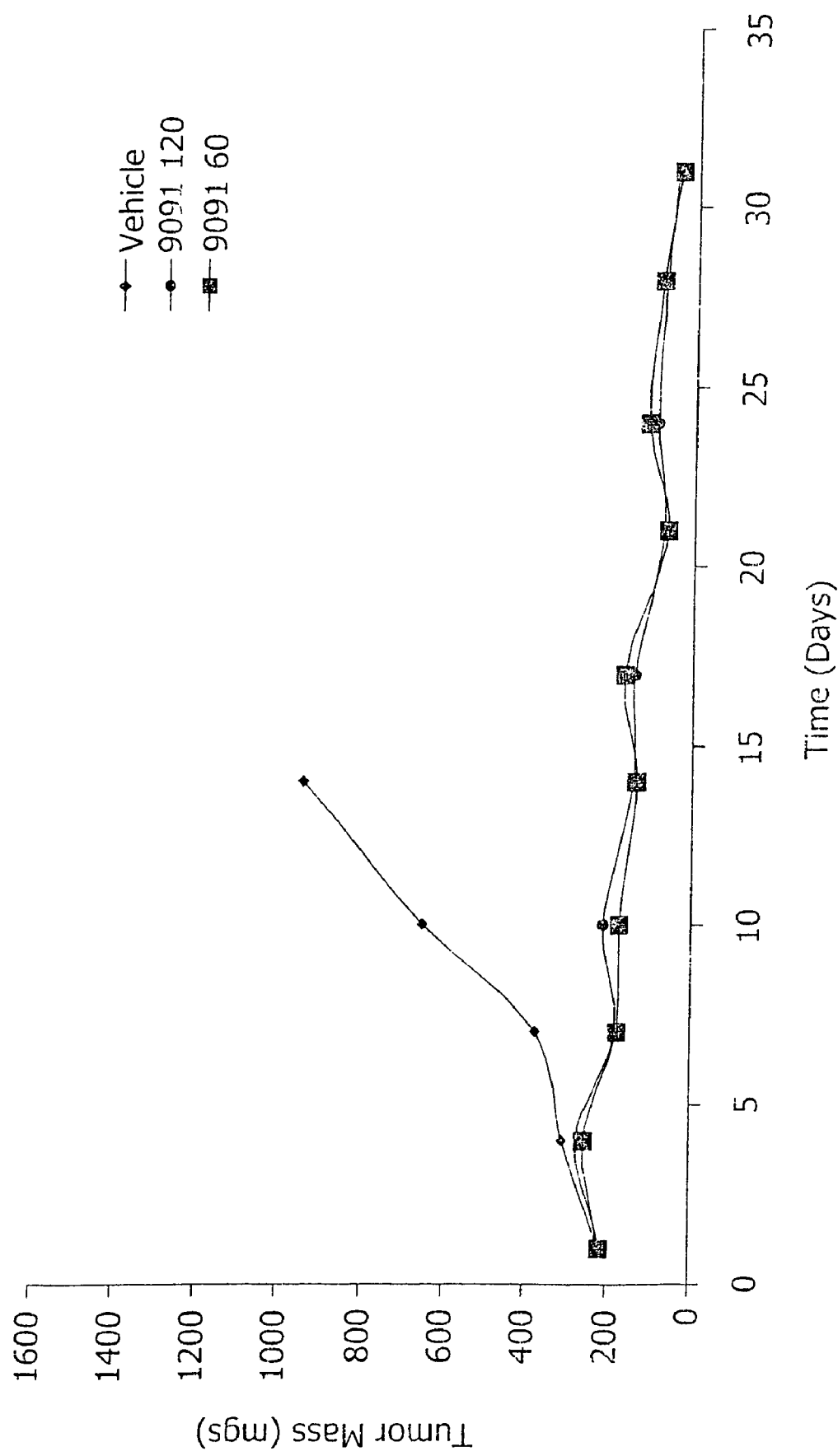
FIG. 4 depicts median tumor growth curves for mice treated with compound 9091 in the Panc-1 study (oral single doses of 60 mg/kg and 120 mg/kg).
Figure 5:
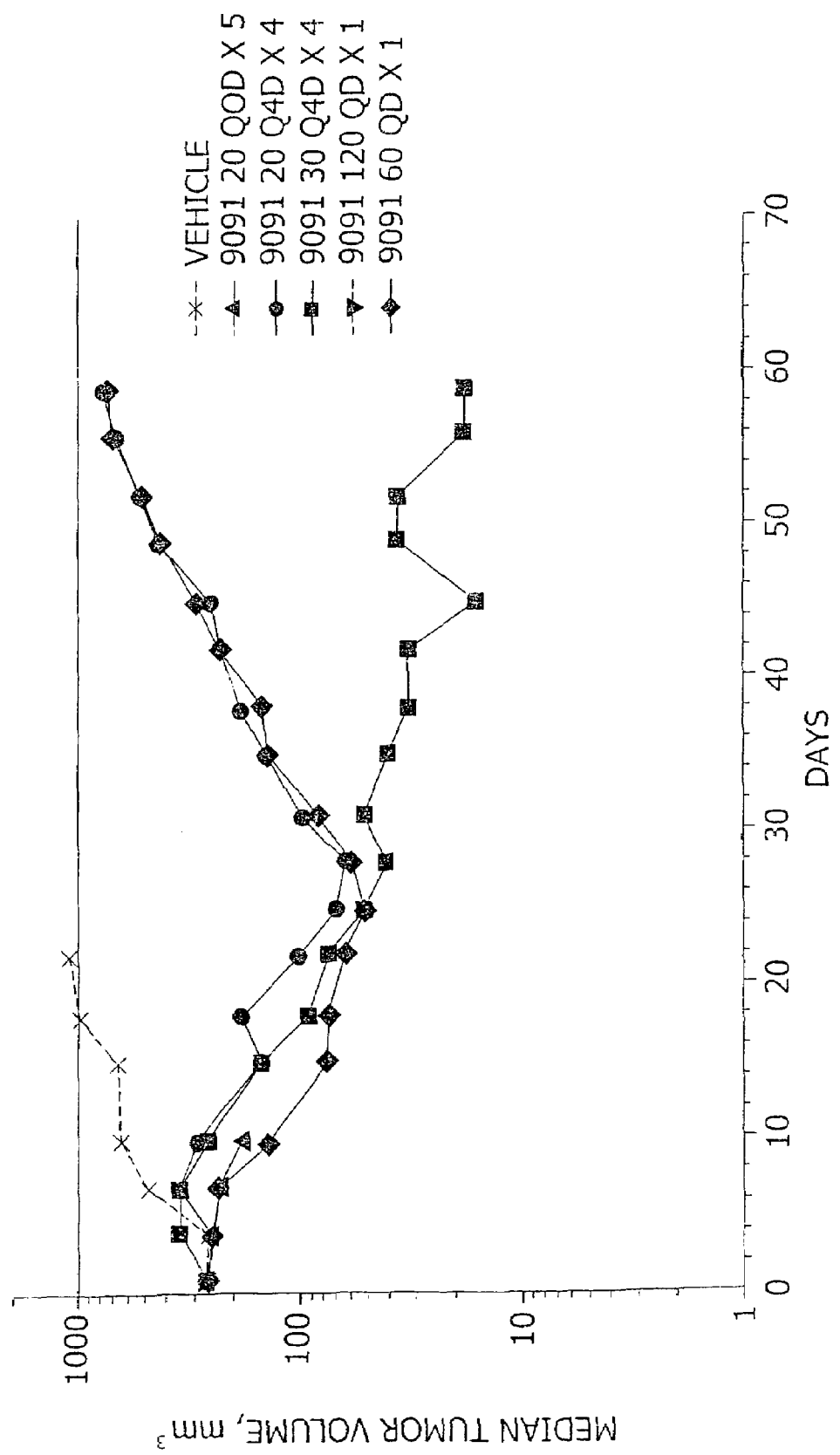
FIG. 5 depicts median tumor growth curve plots for mice treated with i.v. doses of compound 9091 in the HT29 study.
Figure 6:
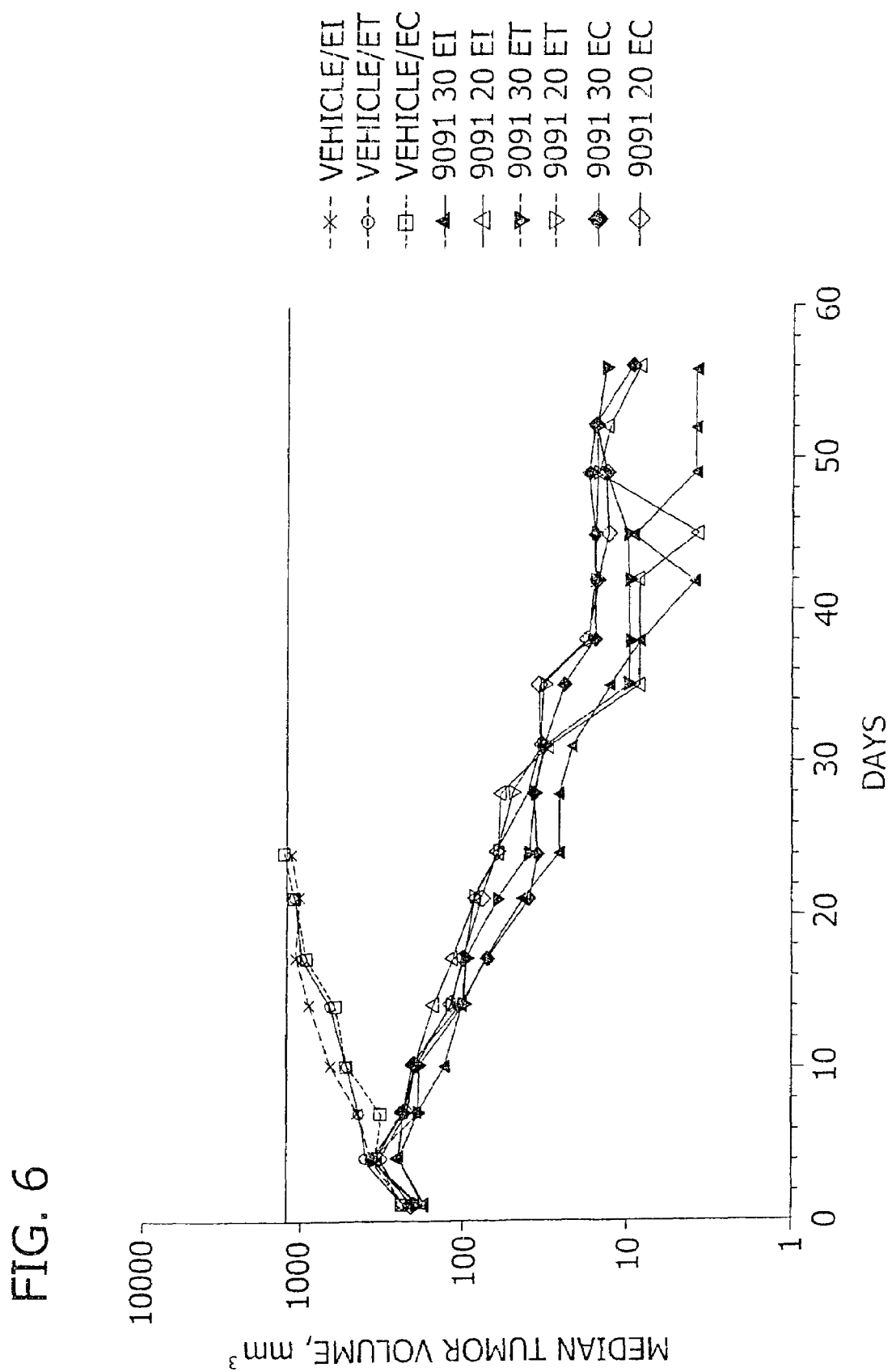
FIG. 6 depicts group median tumor growth curves for mice treated with vehicles or with q4d×4 i.v. doses of compound 9091 in 5% E-95% I-20, 5% ET in Saline, and 5% EC in Saline in the HT29 study; (E—ethanol; I—intralipid; T—tween; C—cremophor; e.g.; 5% EC in saline is 5% ethanol and 5% cremophor in saline).
Figure 7:
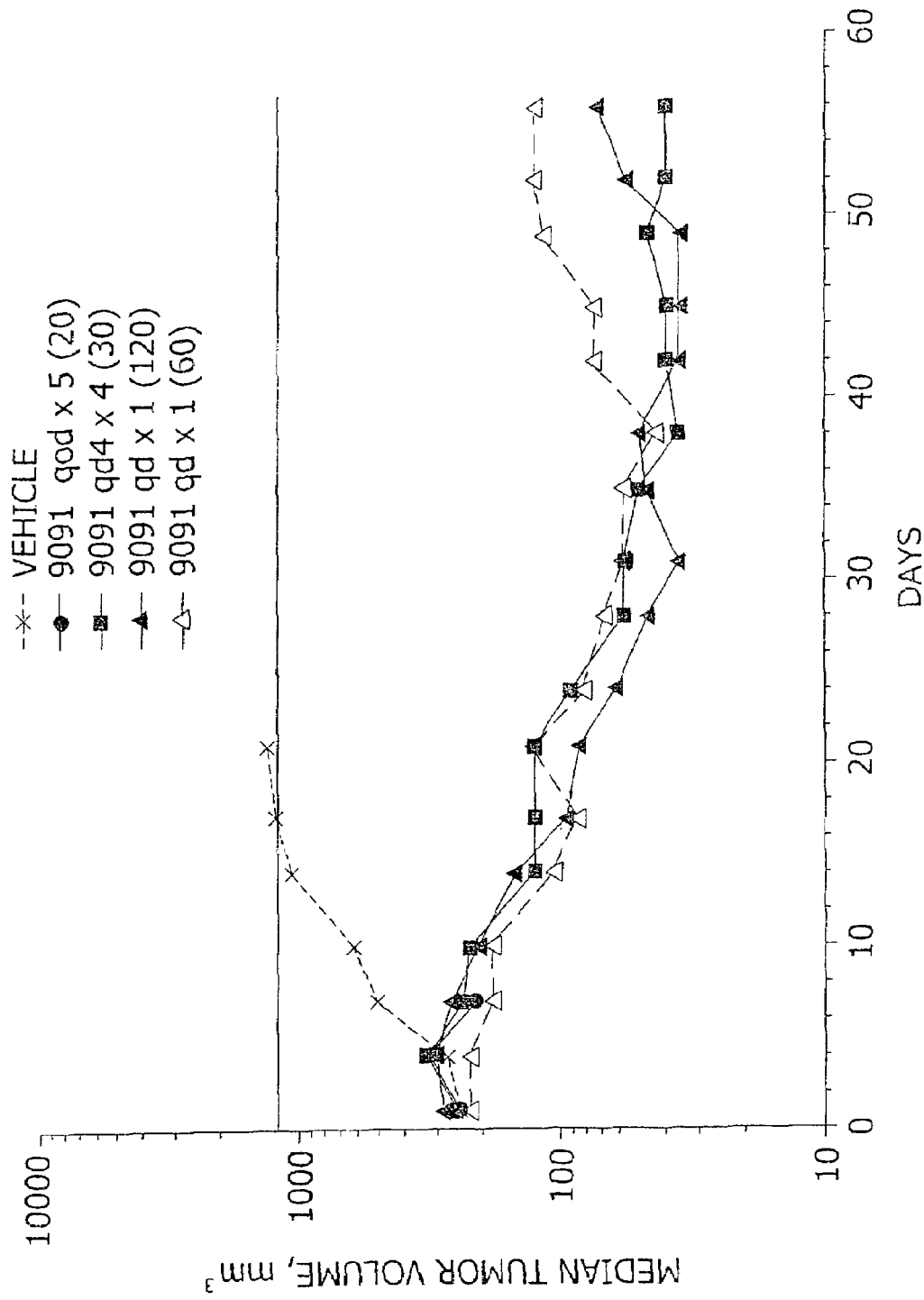
FIG. 7 depicts median tumor growth curves for mice treated with i.v. doses of compound 9091 in the Panc-1 study.

Graphical results of the evaluation of compound 9091 in mouse grafts are presented in FIGS. 1-7.

EXAMPLE 6

In Vivo Toxicity Assessment in Rats

Toxicity was assessed in 250-300 g Sprague-Dawley rats and three rats were used per dose group. Three dose groups of the test compound, (i.e., 3 mg/kg, 9 mg/kg and 12 mg/kg for intravenous administration; 15 mg/kg, 30 mg/kg and 40 mg/kg) and 1 control group constituted a study. Animals were observed and clinical chemistry data collected at days 4 and 10. Rats were euthanized on day 11 and the nerves were excised and fixed upon euthanization for further examination.

Each rat is scored as described below and a final toxicity score that incorporates all parameters is assigned. A dead rat is assigned a score of zero. Table 5 below gives the criteria for how each toxicity parameter contributes to the score. Most of the parameters contribute a positive value towards a total possible score of 130. For body weight, white blood cell, and platelet decreases, recovery is considered. If the parameter does not show recovery, then a −5 is subtracted from the total. The total score is divided by 13 to put it on a scale from 0 to 10. As for the neurotoxicity score, a −10 indicates that axonal degeneration lesions were seen, while a 0 indicates there were no lesions.

TABLE 5

Criteria for Rat Toxicity Scoring

| Observation | Score | | | | Recovery Week 2 | |
|---|---|---|---|---|---|---|
| Neurotoxicity | N (0) 0 | Y (1-4) −10 | | | N | Y |
| Body Weight Loss | ≧20% 0 | ≧15% 5 | ≧10% 10 | <10% 20 | −5 | 0 |
| WBC decrease | ≧50% 0 | ≧25% 5 | ≧10% 10 | <10% 20 | −5 | 0 |
| Platelets decrease | ≧75% 0 | ≧50% 5 | ≧25% 10 | <25% 20 | −5 | 0 |
| AST elevation | ≧2Xcont. 0 | ≧1.5Xcont 5 | ≧1.25Xcont 10 | <1.25Xcont 20 | | |
| ALT elevation | ≧2Xcont 0 | ≧1.5Xcont 5 | ≧1.25Xcont 10 | <1.25Xcont 20 | | |
| BUN elevation | ≧2Xcont 0 | ≧1.5Xcont 5 | ≧1.25Xcont 10 | <1.25Xcont 20 | | |
| Water/Loose Diarrhea | N 5 | Y 0 | | | | |
| Bloody/Mucoid Diarrhea | N 5 | Y 0 | | | | |

Maxium score (each rat) = 130;
Group score = average of 3 rats/13;
Avg = average of 3 groups
Wt Avg = (Σ(dose × grp score))/24
cont—control
AST—Aspartate aminotransferase(AST);
ALT—Alanine aminotransferase;
PTL—Platelet;
BUN—Blood urine nitrogen
WBC—White blood cell A sample of the data for an oral dosage rat toxicity study of compound 9091 is presented in Table 6.

TABLE 6

Sample Inputs into Rat Toxicity Scores; Oral Dosage Study

| Dose/ Rat | Neu Tox | BW | R = Recovery R | WBC | R | Compound 9091 AST | ALT | BUN | PTL | R | L/W Dia | B/M Dia | Total Score | | |
|---|---|---|---|---|---|---|---|---|---|---|---|---|---|---|---|
| High Dose 40 mg/kg | | | | | | | | | | | | | | | |
| Rat 1 | 0 | −5 | 0 | 0 | 20 | 20 | 20 | 5 | 0 | 0 | 0 | 60 | 60 | | |
| Rat 2 | −10 | 0 | 0 | 0 | 20 | 20 | 10 | 20 | −5 | 0 | 0 | 55 | 55 | | |
| Rat 3 | −10 | 0 | −5 | 0 | 20 | 20 | 20 | 20 | 0 | 0 | 0 | 65 | 65 | | |
| | | | | | | | | | | | | AVE | 60 | 180 | 4.62 |
| Mid Dose 30 m g/kg | | | | | | | | | | | | | | 0 | |
| | | | | | | | | | | | | | | 0 | |
| | | | | | | | | | | | | | | 0 | |

TABLE 6-continued

Sample Inputs into Rat Toxicity Scores; Oral Dosage Study

| Dose/ Rat | Neu Tox | BW | R = Recovery | | | | Compound 9091 | | | | L/W | B/M | Total | |
|---|---|---|---|---|---|---|---|---|---|---|---|---|---|---|
| | | | R | WBC | R | AST | ALT | BUN | PTL | R | Dia | Dia | Score | |
| Rat 1 | | 5 | 0 | 0 | 0 | 20 | 20 | 20 | 20 | 0 | 0 | 0 | 85 | 85 |
| Rat 2 | | 10 | 0 | 5 | 0 | 20 | 20 | 20 | 20 | 0 | 0 | 0 | 95 | 95 |
| Rat 3 | −10 | 10 | 0 | 0 | 0 | 20 | 20 | 20 | 20 | 0 | 0 | 0 | 80 | 80 |
| | | | | | | | | | | | | AVE | 86.7 | 260 | 6.67 |
| Low Dose 15 m g/kg | | | | | | | | | | | | | | 0 0 0 |
| Rat 1 | | 20 | 0 | 5 | 0 | 20 | 20 | 20 | 20 | 0 | 0 | 5 | 110 | 110 |
| Rat 2 | −10 | 10 | 0 | 0 | 0 | 20 | 20 | 20 | 20 | 0 | 0 | 5 | 85 | 85 |
| Rat 3 | | 20 | 0 | 0 | 0 | 20 | 20 | 20 | 10 | 0 | 0 | 5 | 95 | 95 |
| | | | | | | | | | | | | AVE | 96.7 | 290 | 7.44 |

The resulting scores from a complete study of oral and two IV dosage regimens in rats are summarized in Table 7 below and compared with a previously disclosed analog, compound 3071. The structure for compound 3071 can be found in Example 9.

TABLE 7

Toxicity Scores from Rat Studies of Compound 9091 (vs. 3071)

| | Tox Score Dose | | | | |
|---|---|---|---|---|---|
| Compound | 3 mg | 9 mg | 12 mg | Average | Weighted Avg |
| IV 3071 | 7.7 | 6 | 3.2 | 5.6 | 4.8 |
| IV 9091 | 9 | 7.1 | 7.8 | 7.9 | 7.7 |
| IV 9091 | 9.5 | 8.1 | 6.8 | 8.1 | 7.6 |
| Compound | 15 mg | 30 mg | 40 mg | Average | Weighted Avg |
| Oral 3071 | 6.2 | 5.1 | 1.5 | 4.3 | 3.6 |
| Oral 9091 | 7.4 | 6.7 | 4.6 | 6.2 | 5.8 |

EXAMPLE 7

In Vivo Efficacy Assessment in Mouse Xenograft Studies

To simplify the interpretation of mouse xenograft studies, an efficacy score was derived from the mouse xenograft studies described in Examples 4 and 5 above.
Score=10*(TWd1−TWdn)/TWd1, where
 TWd1=tumor weight on day 1
 TWDn=lowest tumor weight on day 10 or later Thus the best score for complete regression would be 10. The results for compound 9091 are summarized in Tables 8a and 8b and compared with values for the congeners 3071 and 3102.

TABLE 8A

Efficacy of 9091 vs 3071 in Single Dose Oral Mouse Xenograft Studies at 60 and 120 mg/kg

| Compound | Tumor | Dose | Score |
|---|---|---|---|
| 3071 | Panc-1 | 60 | 5.8 |
| 3071 | Panc-1 | 120 | 7.3 |

TABLE 8A-continued

Efficacy of 9091 vs 3071 in Single Dose Oral Mouse Xenograft Studies at 60 and 120 mg/kg

| Compound | Tumor | Dose | Score |
|---|---|---|---|
| 3071 | HT29 | 60 | 6.3 |
| 3071 | HT29 | 120 | 7.5 |
| 9091 | Panc-1 | 60 | 8.3 |
| 9091 | Panc-1 | 120 | 9.1 |
| 9091 | HT29 | 60 | 4.3 |
| 9091 | HT29 | 120 | 8.7 |

TABLE 8B

Efficacy of 9091 vs 3102 in Single Dose IV Mouse Xenograft Studies

| Compound | Tumor | Dose | Score |
|---|---|---|---|
| 3102 | Panc-1 | 60 | 2.6 |
| 3102 | Panc-1 | 120 | 5.3 |
| 3102 | HT29 | 60 | 1.3 |
| 3102 | HT29 | 120 | 5.3 |
| 9091 | Panc-1 | 60 | 7.7 |
| 9091 | Panc-1 | 120 | 8.6 |
| 9091 | HT29 | 60 | 8 |
| 9091 | HT29 | 120 | 8.7 |

EXAMPLE 9

Comparative Efficacy and Toxicity Data

Additional efficacy data from cell proliferation studies as well as scores from rat toxicity studies are presented in Table 9 for comparable compounds corresponding to the formula

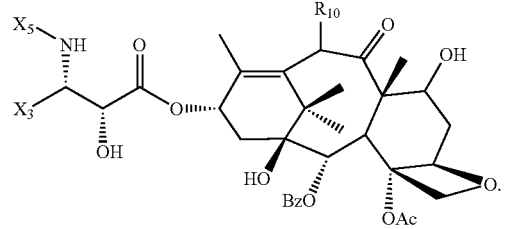

All of the compounds listed in Table 9, with the exception of compound 9091, appear in PCT publication WO 01/57032.

TABLE 9

Comparative Summary of Toxicity Data

| Compound | $X_5$ | $X_3$ | $R_{10}$ | HCT116 $IC_{50}$, nM | VM46 $IC_{50}$, nM | Rat tox score IV | Rat tox score PO |
|---|---|---|---|---|---|---|---|
| paclitaxel | PhCO | Ph | AcO | 2.1 | 20.0 | | |
| docetaxel | tBuOCO | Ph | OH | 0.6 | 6.7 | | |
| 0843 | tBuOCO | 2fu | cproCOO | 0.24 | 0.86 | 0 | 0 |
| 0854 | tBuOCO | 2th | cproCOO | 0.05 | 0.09 | 1 | 0 |
| 2781 | tBuOCO | 3fu | cproCOO | 0.18 | 1.91 | 1 | 0 |
| 2794 | tBuOCO | 3th | cproCOO | 0.28 | 2.03 | | |
| 2802 | tBuOCO | 2py | cproCOO | 0.30 | 3.32 | | |
| 2813 | tBuOCO | 4py | cproCOO | 0.05 | 8.22 | | |
| 3071 | iPrOCO | 2th | cproCOO | 0.17 | 1.51 | 5 | 4 |
| 3102 | iBuOCO | 2fu | cproCOO | 0.33 | 1.49 | 6 | 6 |
| 3129 | iBuOCO | 2th | cproCOO | 1.53 | 2.88 | | |
| 3132 | nPrCO | 2th | cproCOO | 0.37 | 5.33 | | |
| 3677 | EtOCO | 2fu | cproCOO | 0.30 | 18.56 | | |
| 3853 | iPrOCO | 2fu | cproCOO | 0.08 | 0.99 | 1 | 1 |
| 4051 | EtOCO | 2th | cproCOO | 0.30 | 1.62 | | 5 |
| 4062 | nPrCO | 2fu | cproCOO | 0.59 | 7.64 | | |
| 4665 | iBuOCO | 3fu | cproCOO | 2.13 | 28.45 | | |
| 5011 | iBuOCO | 3th | cproCOO | 2.99 | 8.47 | | |
| 9091 | iPrOCO | 2th | cpentCOO | 0.63 | 1.87 | 8, 8 | 6 |

The results of the studies described above indicate that compound 9091 belongs to a class of effective agents against several tumor lines. When compared with congeners, compound 9091 demonstrated the best toxicity profile in rats when administered intravenously. Even though it has a better toxicity profile in the oral rat studies, compound 9091 is more efficacious than compound 3071 in single dose oral xenograft studies, and compound 9091 is much more efficacious than compound 3102 (another congener) in single dose IV xenograft studies at doses of 60 mg/kg and 120 mg/kg.

Compound 9091, therefore, has the potential as a safe and effective antitumor agent for oral and IV administration.

What is claimed is:

1. A method of inhibiting tumor growth in a mammal, said method comprising administering to the mammal a therapeutically effective amount of a pharmaceutical composition comprising a taxane and at least one pharmaceutically acceptable carrier, the taxane having the structure:

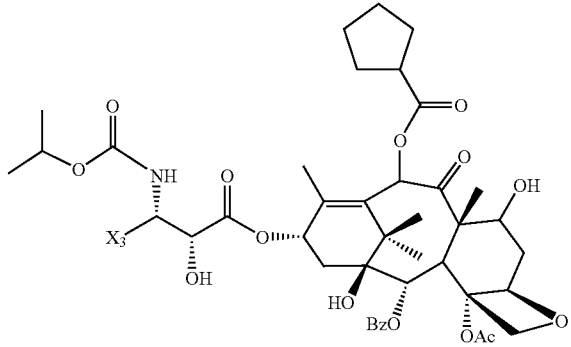

wherein $X_3$ is thienyl, Ac is acetyl, and Bz is benzoyl.

2. The method of claim 1 wherein said pharmaceutical composition is administered orally.

3. The method of claim 1 wherein said pharmaceutical composition is administered parenterally.

4. The method of claim 3 wherein the mammal is pretreated with dexamethasone, diphenhydramine, or other agent that minimizes adverse reactions from the administration of the pharmaceutical composition and the pharmaceutical composition comprises a surfactant.

5. The method of claim 4 wherein the surfactant is polysorbate 80, polyethoxylated castor oil, or a combination thereof.

6. The method of claim 1 wherein the tumor is breast, lung, pancreas, colon, ovarian, or prostate carcinoma.

7. The method of claim 6 wherein the tumor is Panc-1 pancreatic adenocarcinoma or HT-29 colon carcinoma.

8. The method of claim 1 wherein the tumor is resistant to taxol.

9. The method of claim 8 wherein the tumor is human colon carcinoma.

10. The method of claim 9 wherein the tumor is VM46 Human Colon Carcinoma.

11. The method of claim 9 wherein the tumor is DLD-1 Human Colon Carcinoma.

12. The method of claim 1 wherein the tumor is human pancreatic carcinoma or human colon carcinoma.

13. The method of claim 1 wherein the tumor is human colon carcinoma.

14. The method of claim 1 wherein the tumor is human pancreatic carcinoma.

15. The method of claim 13 wherein the tumor is HT-29 colon carcinoma, VM46 colon carcinoma, DLD-1 colon carcinoma, or HCT-116 colon carcinoma.

16. The method of claim 14 wherein the tumor is Panc-1 pancreatic carcinoma.

17. The method of claim 1 wherein the taxane has the structure:

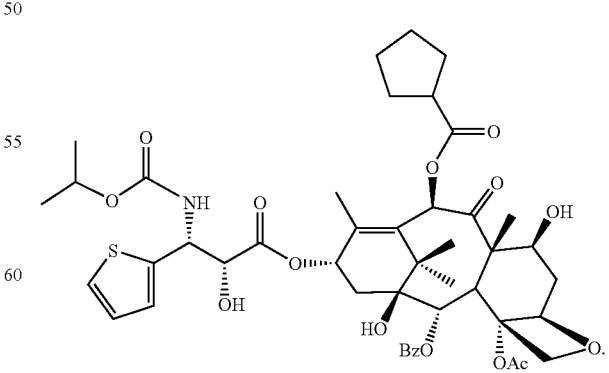

* * * * *

UNITED STATES PATENT AND TRADEMARK OFFICE
CERTIFICATE OF CORRECTION

PATENT NO. : 7,589,111 B2  Page 1 of 1
APPLICATION NO. : 11/057703
DATED : September 15, 2009
INVENTOR(S) : Holton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1184 days.

Signed and Sealed this

Twenty-first Day of September, 2010

David J. Kappos
*Director of the United States Patent and Trademark Office*